US009233032B2

(12) United States Patent
Yamanaka et al.

(10) Patent No.: US 9,233,032 B2
(45) Date of Patent: Jan. 12, 2016

(54) LIQUID-PERVIOUS SHEET AND METHOD OF MAKING THE SAME

(75) Inventors: Yasuhiro Yamanaka, Kagawa (JP); Naoto Ohashi, Kagawa (JP)

(73) Assignee: Unicharm Corporation, Ehime (JP)

( * ) Notice: Subject to any disclaimer, the term of this patent is extended or adjusted under 35 U.S.C. 154(b) by 60 days.

(21) Appl. No.: 13/882,090

(22) PCT Filed: Nov. 30, 2011

(86) PCT No.: PCT/JP2011/006725
§ 371 (c)(1),
(2), (4) Date: Apr. 26, 2013

(87) PCT Pub. No.: WO2012/073514
PCT Pub. Date: Jun. 7, 2012

(65) Prior Publication Data
US 2013/0236700 A1 Sep. 12, 2013

(30) Foreign Application Priority Data

Nov. 30, 2010 (JP) .................................. 2010-267894
Nov. 8, 2011 (JP) .................................. 2011-244092

(51) Int. Cl.
*A61F 13/511* (2006.01)
*A61F 13/15* (2006.01)
(Continued)

(52) U.S. Cl.
CPC ..... *A61F 13/51108* (2013.01); *A61F 13/15731* (2013.01); *A61F 13/5116* (2013.01);
(Continued)

(58) Field of Classification Search
CPC .......................... B32B 23/10; A61F 13/51104
USPC .......................................................... 264/505
See application file for complete search history.

(56) References Cited

U.S. PATENT DOCUMENTS 3,766,922 A * 10/1973 Krusko ............. A61F 13/15626
19/148
2003/0167044 A1* 9/2003 Toyoshima et al. ........... 604/367
(Continued)

FOREIGN PATENT DOCUMENTS

| JP | 58-132155 | 8/1983 |
| JP | 2008-025079 | 2/2008 |

(Continued)

OTHER PUBLICATIONS

Nishitani K., Sagisaka M., Oba K., Yokoe K. "Surface Sheet for Absorbent Article, its Manufacturing Method, and Absorbent Article using the Surface Sheet"; JP2009-273722A (machine translation), Nov. 26, 2009.*

(Continued)

*Primary Examiner* — David Sample
*Assistant Examiner* — Donald M Flores, Jr.
(74) *Attorney, Agent, or Firm* — Brinks Gilson & Lione

(57) ABSTRACT

The present invention aims to provide a liquid-pervious sheet suitable to be used as a liquid-pervious topsheet of a bodily fluid-absorbent wearing article. One surface 58 of both surfaces 57, 58 of a liquid-pervious sheet 11 is formed with crests 61 and troughs 62 extending in parallel to one another in a longitudinal direction A and alternate in a transverse direction B. The one surface 58 is additionally formed at least in the respective crests 61 with a series of compressed debosses 70. In the respective compressed debosses 70, thermoplastic synthetic fibers forming the liquid-pervious sheet 11 more densely gather together than in zones surrounding the respective compressed debosses 70 and thereby maintain initial fiber formation of the individual thermoplastic synthetic fibers.

16 Claims, 12 Drawing Sheets

(51) Int. Cl.
- *A61F 13/513* (2006.01)
- *D04H 1/44* (2006.01)
- *D04H 1/558* (2012.01)
- *D04H 1/559* (2012.01)
- *D04H 1/62* (2006.01)

(52) U.S. Cl.
CPC ..... *A61F 13/51104* (2013.01); *A61F 13/51305* (2013.01); *D04H 1/44* (2013.01); *D04H 1/558* (2013.01); *D04H 1/559* (2013.01); *D04H 1/62* (2013.01); *A61F 2013/15829* (2013.01); *A61F 2013/15983* (2013.01); *A61F 2013/51178* (2013.01); *Y10T 428/24587* (2015.01); *Y10T 428/24603* (2015.01)

(56) References Cited

U.S. PATENT DOCUMENTS

| | | | |
|---|---|---|---|
| 2004/0142151 A1* | 7/2004 | Toyoshima et al. | 428/172 |
| 2007/0298671 A1* | 12/2007 | Noda et al. | 442/334 |
| 2011/0118691 A1 | 5/2011 | Nishitani et al. | |
| 2012/0196091 A1* | 8/2012 | Mizutani et al. | 428/171 |
| 2013/0178815 A1* | 7/2013 | Ohashi et al. | 604/380 |

FOREIGN PATENT DOCUMENTS

| | | | |
|---|---|---|---|
| JP | 2008-080150 | 4/2008 | |
| JP | 2009/000173 | 1/2009 | |
| JP | 2009-233099 | 10/2009 | |
| JP | 2009-273722 | 11/2009 | |
| JP | 2009273722 A * | 11/2009 | A61F 13/49 |
| JP | 2010-158488 | 7/2010 | |
| WO | WO 2008/146541 A1 | 12/2008 | |
| WO | WO 2008/156075 A1 | 12/2008 | |
| WO | WO 2011/043180 A1 | 4/2011 | |
| WO | WO 2012/043843 A1 | 4/2012 | |

OTHER PUBLICATIONS

International Search Report from corresponding PCT application No. PCT/JP006725 dated Feb. 21, 2012 (2 pgs).

European extended Search Report from corresponding European Application No. 11844605.3 dated Nov. 14, 2014 (7 pgs).

* cited by examiner (a)

(b)

(a)

(b)

LIQUID-PERVIOUS SHEET AND METHOD OF MAKING THE SAME

TECHNICAL FIELD

The present disclosure relates to liquid-pervious sheets suitable as topsheets of bodily fluid-absorbent wearing articles such as disposable diapers or menstruation napkins, and methods of making the same.

BACKGROUND

Conventionally, bodily fluid-absorbent wearing articles such as disposable diapers or menstruation napkins are known including a liquid-pervious topsheet, a liquid-impervious backsheet and a bodily fluid-absorbent core interposed between the top- and backsheets. It is known to form the topsheet on one of its surfaces with a first group of crests and troughs alternately arranged to extend in parallel in one direction, and with another group of crests and troughs alternately arranged to extend in parallel in a direction orthogonal to the former group of crests and troughs. It is also known to utilize such a topsheet in a manner such that the crests and the troughs face the wearer's skin.

For example, JP 1983-132155 A (PTL 1) discloses a liquid-pervious nonwoven fabric suitable for use as a topsheet in a disposable diaper or the like. This nonwoven fabric has crests and troughs extending in parallel in a machine direction in the manufacturing process of the nonwoven fabric. The density of the nonwoven fabric is higher in the troughs than in the crests.

JP 2008-25079A (PTL 2) also discloses a liquid-pervious nonwoven fabric suitable for use as a topsheet in a disposable diaper or the like. This nonwoven fabric is generally flat on one surface thereof and formed on the other surface with crests and troughs extending in parallel in a machine direction and similar crests and troughs extending in parallel in a cross direction orthogonal to the machine direction. The nonwoven fabric has a higher density in the crests than that in the troughs.

WO 2008-146541 A1 (PTL 3) discloses a laminate of sheet elements. According to one embodiment, the laminate consists of a first sheet element and a second sheet element laminated together, and both the first and second sheet elements contain thermoplastic fibers. The first sheet element is formed with a plurality of through-holes having the same longitudinal direction. In addition to the through-holes, the first sheet element is formed with a plurality of grooves along the longitudinal direction of the through-holes. The first sheet element and the second sheet element are fusion bonded to each other in a plurality of joint debosses.

CITATION LIST

Patent Literature

{PTL 1} JP 1983-132155 A
{PTL 2} JP 2008-25079 A
{PTL 3} WO 2008-146541 A1

SUMMARY

Technical Problem

When the nonwoven fabrics disclosed in PTL 2 and PTL 3, both having crests and troughs extending in parallel in one direction, are used as liquid-pervious topsheets in bodily fluid-absorbent wearing articles, the crests function to create a soft feeling to the wearer's skin when the topsheet comes in contact with the wearer's skin. As disclosed in PTL 1, on the assumption that a fiber density is higher in the troughs than in the crests, bodily fluids once having been absorbed by the crests can move smoothly to the troughs and then quickly move from the troughs to the absorbent structure. In consequence, after bodily fluids have been discharged, the topsheet can quickly restore a dry condition. However, some of the fibers forming the crests extend in parallel to the direction in which the crests extend; bodily fluids are difficult to disperse along these fibers to be quickly absorbed by the absorbent structure and are apt to stay on the topsheet. In consequence, the bodily fluid-absorbent wearing article may create a wet feeling against the wearer for a long period after excretion of bodily fluids.

Solution to Problem

In a first aspect of the present invention, a liquid-pervious sheet is provided. In a second aspect of the present invention, a method of making this liquid-pervious sheet is provided.

The first aspect of the present invention provides a liquid-pervious sheet having a longitudinal direction, a transverse direction and a thickness direction being orthogonal to one another, includes a nonwoven fabric of thermoplastic synthetic fibers wherein both surfaces of the liquid-pervious sheet intersect with the thickness direction and extend in the longitudinal direction and the transverse direction; and one of the surfaces is formed with crests and troughs extending in the longitudinal direction and alternating in the transverse direction to form an undulated surface having repeated undulations; the other of the surfaces being formed to be a flat surface.

In this liquid-pervious sheet, at least in the crests, the undulated surface includes dot-like debosses formed by locally compressing the nonwoven fabric from the undulated surface toward the opposite flat surface. The thermoplastic synthetic fibers in the nonwoven fabric more densely gather together in the debosses than in zones surrounding the respective debosses wherein the fiber-form of each of the thermoplastic fibers is maintained.

The second aspect of the present invention provides a method of making a liquid-pervious sheet having a longitudinal direction, a transverse direction and a thickness direction being orthogonal to one another and includes a nonwoven fabric made of thermoplastic synthetic fibers wherein both surfaces of the liquid-pervious sheet intersect with the thickness direction and extend in the longitudinal direction and the transverse direction; and one of the both surfaces is formed with crests and troughs extending in the longitudinal direction and alternating in the transverse direction to form an undulated surface having repeated undulations; the other of the both surfaces being formed to be a flat surface.

The method comprises the following steps:

a. continuously feeding a web as mass of thermoplastic synthetic fibers loaded on an air-permeable support means and in a machine direction and subjecting the web to pressurized air jets or pressurized water jets ejected by a series of nozzles arranged in a cross direction intersecting with the machine direction above the support means, so that the pressurized air or the pressurized water is directed from one surface of the web to the other surface, to form the one surface of the web with crests and troughs extending in parallel to one another in the machine direction and alternating in the cross direction to form repeated undulations;

b. feeding the web formed with the crests and the troughs into a clearance between a pair of debossing rolls including a roll having a smooth peripheral surface and a roll having a series of bosses on a peripheral surface thereof so that the bosses may work on the web in a direction from the undulated surface toward the opposite surface thereof and thereby locally compressing the web from the undulated surface toward the opposite surface thereof to form dot-like debosses at least in the crests; and c. keeping the bosses at a temperature in a range to maintain a surface temperature of the bosses without melting the surfaces of the thermoplastic synthetic fibers.

Advantageous Effects of Invention

According to the first aspect of the present invention, the liquid-pervious sheet includes the compressed debosses at least in the crests. In the respective compressed debosses, the thermoplastic synthetic fibers in the nonwoven fabric forming the liquid-pervious sheet more densely gather together than in the zones surrounding the respective compressed debosses and thereby maintain the initial fiber formation thereof. Consequently, bodily fluids once absorbed by the crests move smoothly not only to the troughs but also to the compressed debosses and thereby bodily fluids should stay in the respective crests can be effectively alleviated.

In the method of making the liquid-pervious sheet according to the present invention on the second aspect thereof, the surface temperature of the bosses is kept in a range of temperature where the surfaces of the thermoplastic synthetic fibers in the nonwoven fabric should not be fused. Consequently, in the respective compressed debosses formed by these bosses, the thermoplastic synthetic fibers are kept in close contact with one another but not fusion-bonded together.

DESCRIPTION OF EMBODIMENTS

Details of a liquid-pervious sheet and a method of making the same will be more fully understood from the description given hereunder with reference to the accompanying drawings.

Figure 1:
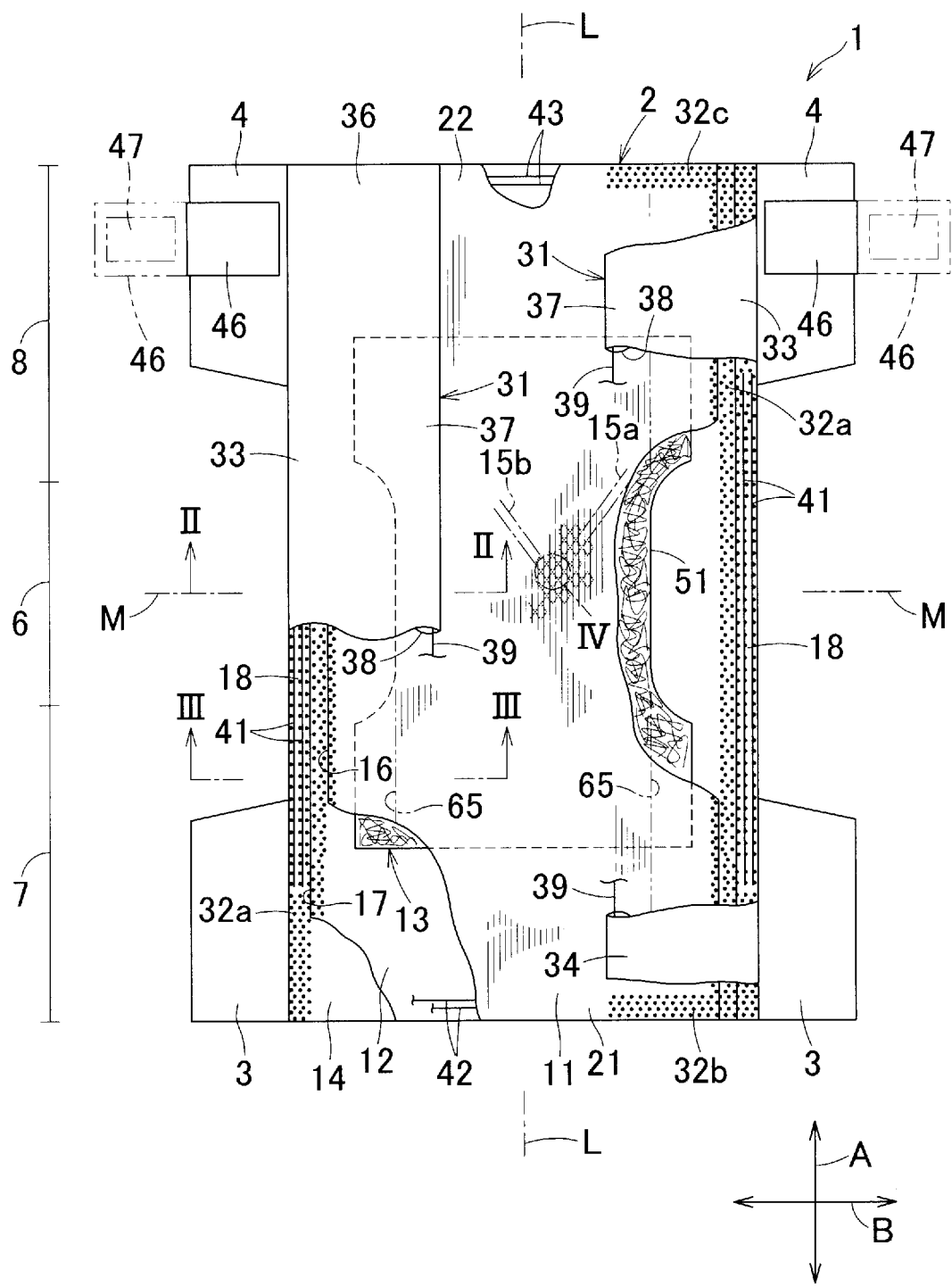
FIG. 1
A partially cutaway plan view of a disposable diaper.

Referring to FIG. 1, a diaper 1 has a longitudinal direction A, a transverse direction B and a thickness direction C (See FIG. 2) which are orthogonal one another. It should be understood that the longitudinal direction A is sometimes designated as a front-back direction and the transverse direction B is sometimes designated as a width direction in the description given hereunder. The diaper 1 includes a rectangular chassis 2 which is longer in the longitudinal direction A than in the transverse direction B, a pair of front wings 3 attached to a front section to extend outward in the transverse direction B and a pair of rear wings 4 attached to a rear section of the chassis to extend outward in the transverse direction B. In the longitudinal direction A of the chassis 2, a crotch region 6 is defined between the front wings 3 and the rear wings 4, a front waist region 7 extends forward from the crotch region 6 and a rear waist region 8 extend rearward from the crotch region 6.

The chassis 2 includes a liquid-pervious topsheet 11, a liquid-impervious backsheet 12 and a bodily fluid-absorbent core 13 interposed between the top- and backsheets 11, 12 wherein the backsheet 12 is covered with an outer sheet 14 formed of a nonwoven fabric of thermoplastic synthetic fibers assuring a comfortable feeling to the wearer's skin. The topsheet 11 and the backsheet 12 extend outward beyond a peripheral edge 51 of the core 13 and are bonded together with hot melt adhesives (not shown) outboard of the peripheral edge 51 of the core 13. In this embodiment, respective dimensions of the top- and backsheets 11, 12 are the same in the longitudinal direction A, but in the transverse direction B, the backsheet 12 extends outward beyond side edges 16 of the topsheet 11. The outer sheet 14 having the same dimension as that of the backsheet 12 in the longitudinal direction A extends outward in the transverse direction B beyond the side edges 17 of the backsheet 12. Portions of these topsheet 11, backsheet 12 and outer sheet 14 extending outward beyond the peripheral edge 51 of the core 13 cooperate together to define opposite side edges 18 and front and rear ends 21, 22 of the chassis 2. The respective side edges 18 are provided with containment flaps 31 formed of sheet strips which are elongated in the longitudinal direction A. Each of the containment flaps 31 has a proximal edge 33 bonded to the associated side edge 18 with hot melt adhesives 32a, a front end 34 and a rear end 36 respectively bonded to the front end 21 and to the rear end 22 with hot melt adhesives 32b, 32c and a free edge 37 lying inboard of the proximal edge 33 and overlapping the topsheet 11 in a manner that the free edge 37 can be spaced apart upward from the topsheet 11. A distal end of the free edge 37 forms a sleeve 38 and an elastic member 39 is attached under tension to an inner surface of this sleeve 38 with hot melt adhesives (not shown). A plurality of dashed-dotted lines 15a, 15b indicated on the topsheet 11 represents rows of a series of compressed zones 70 (See FIGS. 4 through 6) formed on the topsheet 11 as will be described in more detail.

Along the opposite side edges 18 of the chassis 2, leg elastic members 41 extending in the longitudinal direction A under tension are secured between the outer sheet 14 and the proximal edges 33 of the respective containment flaps 31 and attached to the outer sheet 14 with hot melt adhesives (not shown).

Along the front end 21 of the chassis 2, a front waist elastic member 42 extending in the transverse direction B under tension is secured between the topsheet 11 and the backsheet 12 with hot melt adhesives (not shown). In a similar fashion, a rear waist elastic member 43 extending in the transverse direction B under tension is secured between the topsheet 11 and the backsheet 12 with hot melt adhesives (not shown).

As has previously been described, the chassis 2 is provided on the opposite side edges 18 in the front waist region 7 with a pair of the front wings 3, respectively, to extend outward from the side edges 18 in the transverse direction B and on the opposite side edges 18 in the rear waist region 8 with a pair of the rear wings 4, respectively, to extend outward from the side edges 18 in the transverse direction B. The respective rear wings 4 are provided with tape fasteners 46 adapted to be extended in the transverse direction B as indicated by imaginary lines when the diaper 1 is put on the wearer's body and to be detachably fastened to the outer surface of the chassis 2 or the outer surface of the front wings 3 with pressure-sensitive adhesive 47.

Figure 2:
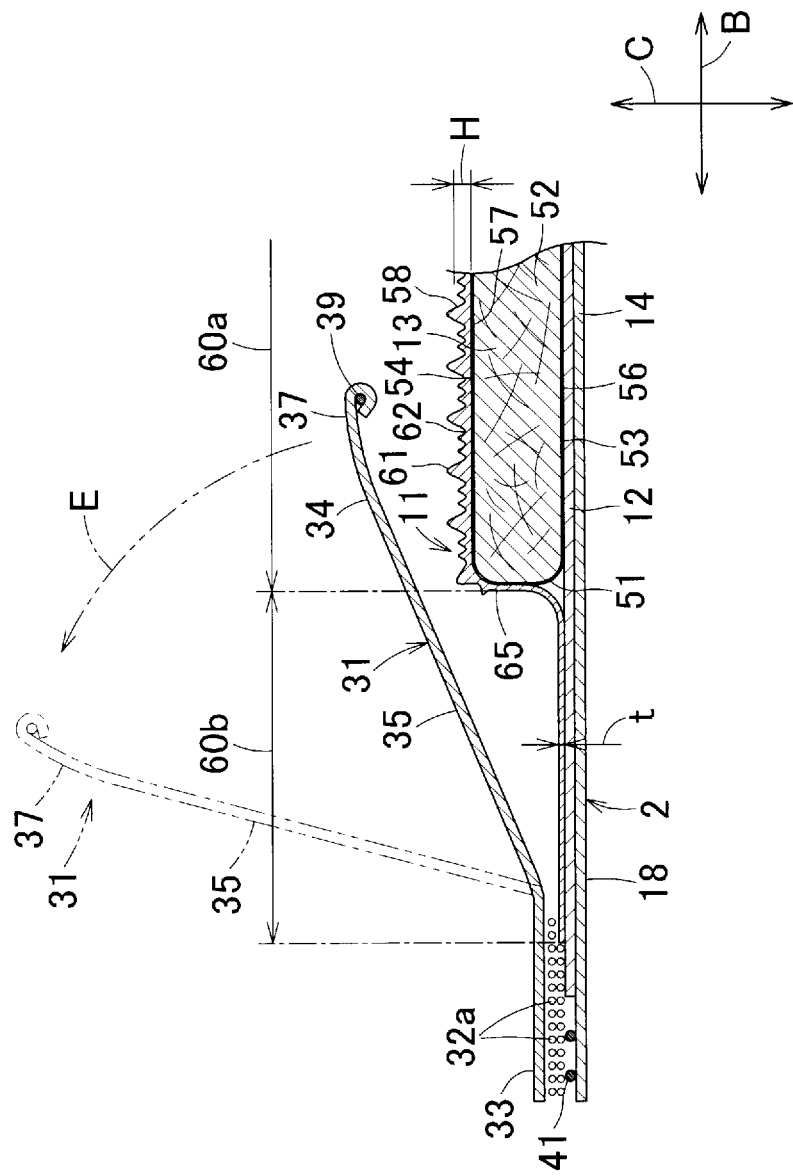
FIG. 2
A sectional view of the diaper of FIG. 1 taken along line II-II in FIG. 1.

The diaper 1 including the chassis 2 has a planar shape which is symmetric about a center line L bisecting a width dimension of the chassis 2. The elastic members 39 for the containment flaps 31 contract as the diaper 1 is curved in a U-shape in the longitudinal direction A with the topsheet 11 inside, and under contraction of the elastic members 39 for the containment flaps 31, the free side edges 37 of the containment flaps 31 are spaced apart upward from the topsheet 11 and the containment flaps 31 raise themselves on the topsheet 11 as is illustrated in FIG. 2. The containment flaps 31 in this posture function to help prevent bodily fluids, flowing on the topsheet 11 in the transverse direction B, from leaking out of the diaper 1.

Referring to FIG. 2, a thickness direction of the diaper 1 is denoted by double-headed arrow C. The core 13 lies at least in a middle zone of the crotch region 6 in the transverse direction B is composed, for example, of a liquid-absorbent material 52 such as fluff wood pulp fibers and/or super-absorbent polymer particles wrapped with a wrapping sheet 53. The wrapping sheet 53 may be formed, for example, of a tissue paper or a liquid-pervious nonwoven fabric. The wrapping sheet 53 is liquid-pervious, preferably not only liquid-pervious but also liquid-absorbent, more preferably has a dispersing property also. An upper surface 54 defined by the wrapping sheet 53 is covered with the topsheet 11 and a lower surface 56 defined by the wrapping sheet 53 is covered with the backsheet 12. Along the opposite side edges 18 of the chassis 2 formed of the topsheet 11, the backsheet 12 and the outer sheet 14, the proximal side edges 33 of the containment flaps 31 may be bonded to the topsheet 11, the backsheet 12 and the outer sheet 14 with, for example, hot melt adhesives 32a. In each of the containment flaps 31, the free side edge 37 and an intermediate section 35 between the free side edge 37 and the proximal side edge 33 take together a posture as indicated by imaginary lines when the containment flap 31 is spaced apart upward from the topsheet 11.

Referring to FIG. 2, the topsheet 11 has a lower surface 57 facing the core 13 and an upper surface 58 facing away from the core 13, wherein the lower surface 57 is generally flat. The upper surface 58 has a central zone 60a defined inboard of the peripheral edge 51 of the core 13 in the crotch region 6, which central zone 60a may be formed with crests 61 and troughs 62 alternately arranged in the transverse direction B (See FIGS. 4 through 7 also); and lateral zones 60b extending outward in the transverse direction B beyond the peripheral edge 51, which lateral zones 60b are flat except regions sharing borders with the peripheral edge 51. A thickness t of the lateral zones 60b may be smaller than a height H of the crests 61 in the central zone 60a. The proximal side edges 93 of the containment flaps 31 may be bonded to the flat lateral zones 60b of the topsheet 11. The central zone 60a of the topsheet 11 smoothly comes in contact with the wearer's skin at the respective crests 61 but not at the troughs 62, and at debosses 70 described below. In consequence, along the respective troughs 62, air-channels extending in the longitudinal direction A are defined between the wearer's skin and the topsheet 11. In FIG. 2, a boundary zone 65 between the central zone 60a and the lateral zones 60b is indicated by an imaginary line.

Figure 3:
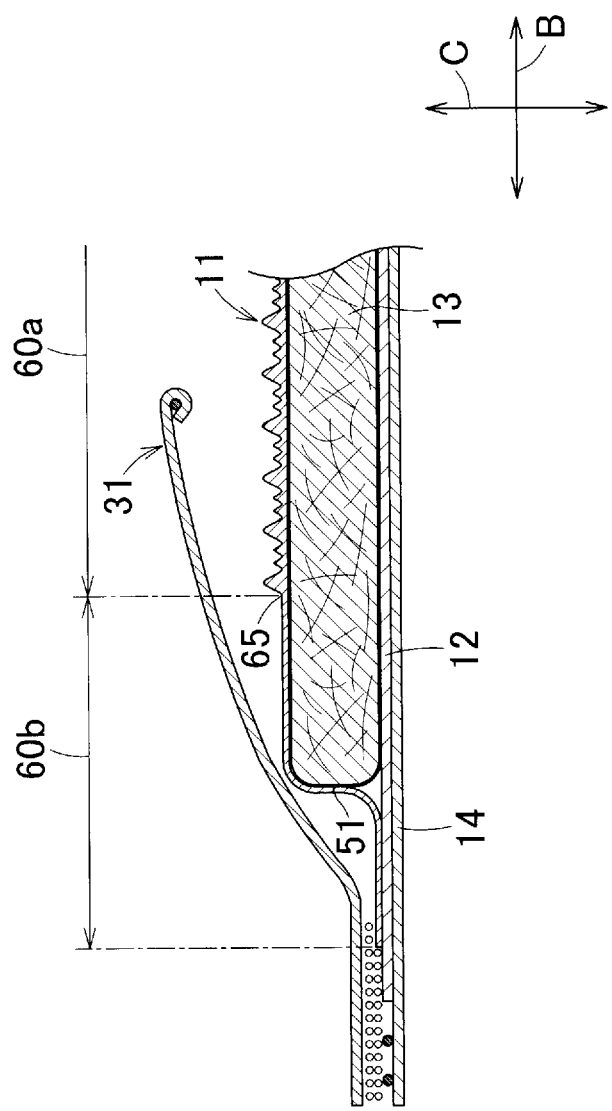
FIG. 3
A sectional view of the diaper of FIG. 1 taken along line III-III in FIG. 1.

Referring to FIG. 3, the core 13 has a shape recessed inwardly in the crotch region 6 and projected outwardly wide in vicinities of the front waist region 7 and the rear waist region 8 as indicated by an imaginary line in FIG. 1. Line III-III extends across the core 13 in its relatively wide portion. The boundary zone 65 between the central zone 60a and the lateral zones 60b extends rectilinearly in the longitudinal direction A, in parallel to the center line L (See FIG. 1). The boundary line 65 is adjacent to the peripheral edge 51 of the core 13 in FIG. 2 but spaced apart from the peripheral edge 51 as the peripheral edge 51 is biased outward in the transverse direction B in FIG. 3. As will be apparent from FIGS. 2 and 3, the flat lateral zones 60b of the topsheet 11 are defined outboard of at least partial segments of the peripheral edge 51 extending in the longitudinal direction A of the core 13, more specifically, outboard of the segments of the peripheral edge 51 defining the narrowest sections of the core 13.

Figure 4:
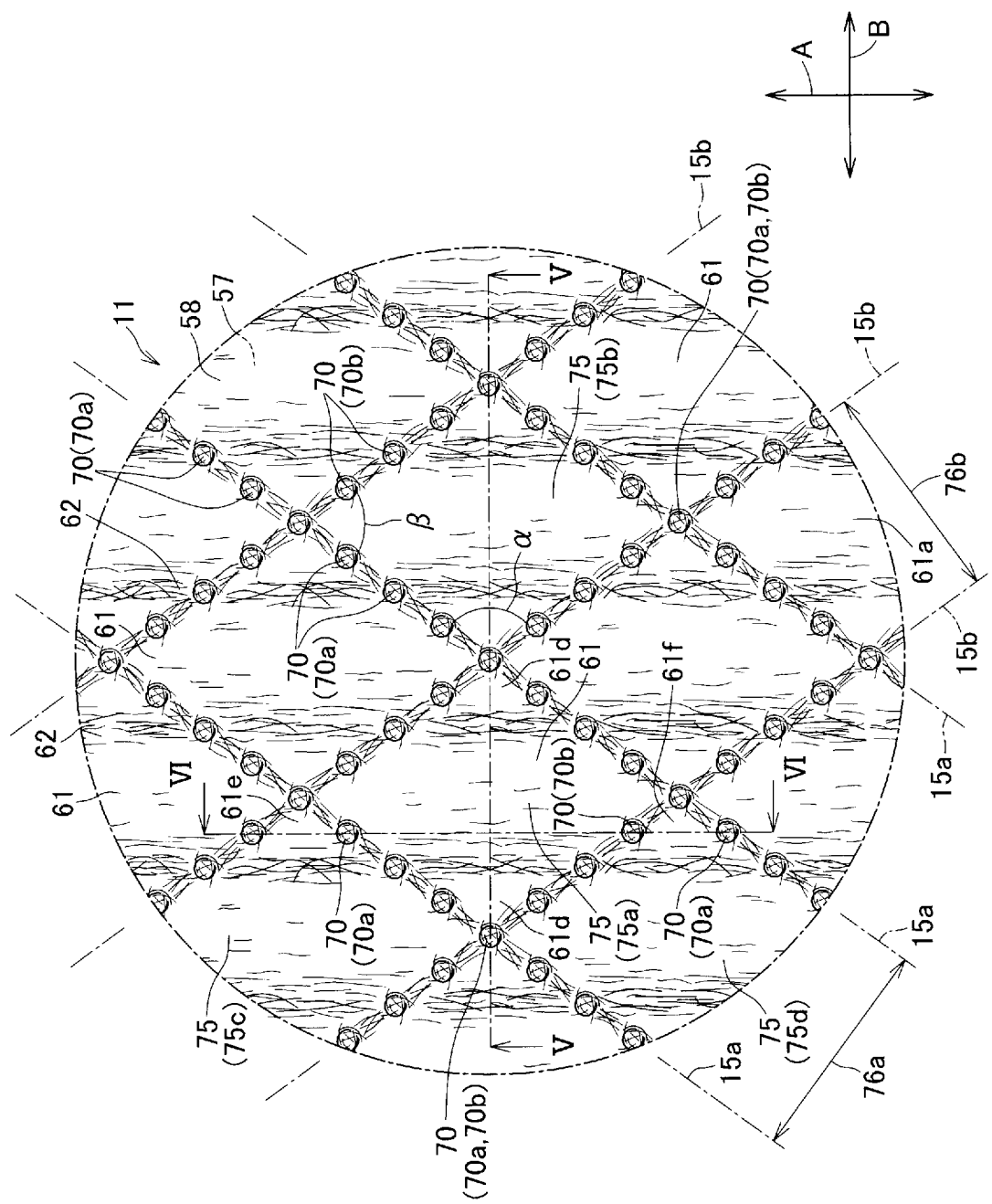
FIG. 4
A scale-enlarged diagram of the diaper of FIG. 1 illustrating an encircled zone IV in FIG. 1.
Figure 5:
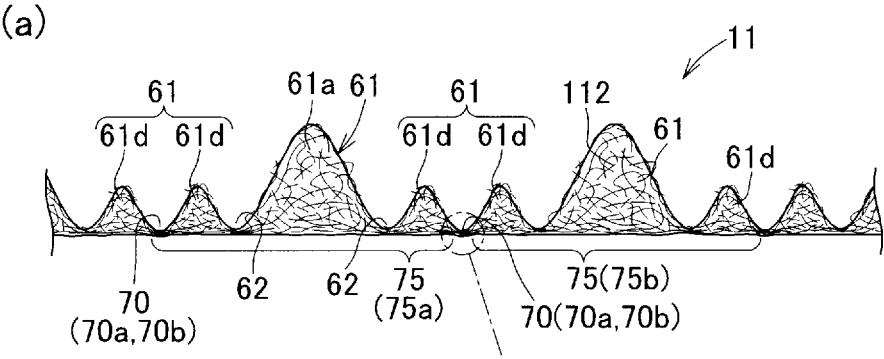
FIG. 5
(a) A sectional view of the diaper of FIG. 1 taken along line V-V in FIG. 4. (b) A partially scale-enlarged diagram of FIG. 5(a).
Figure 5:
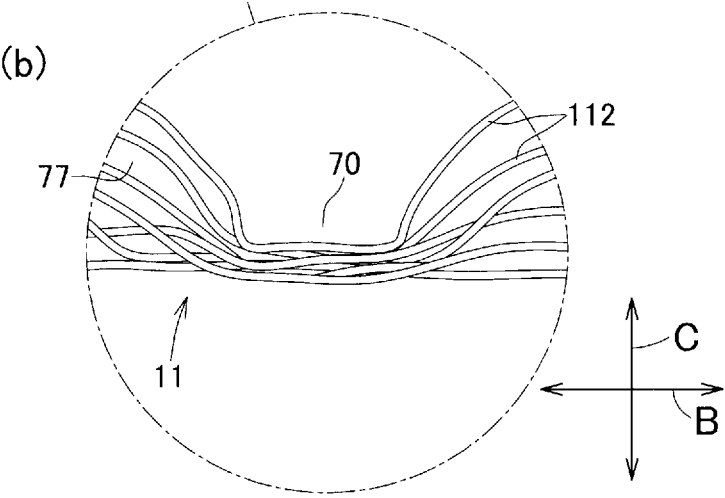
Figure 6:
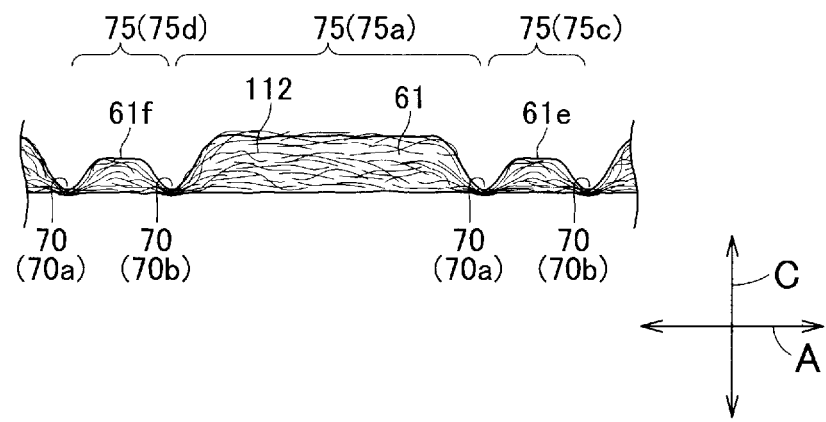
FIG. 6
A sectional view of the diaper of FIG. 1 taken along line VI-VI in FIG. 4.

FIG. 4 is a scale-enlarged diagram illustrating an encircled zone IV in FIG. 1, FIG. 5 is a sectional view taken along line V-V in FIG. 4 and FIG. 6 is a sectional view taken along line VI-VI in FIG. 4. Referring to FIG. 4, the topsheet 11 is formed on its upper surface 58 with a series of compressed debosses 70. These compressed debosses 70 are formed by compressing the topsheet 11 from the upper surface 58 toward the lower surface 57 and includes a series of compressed debosses 70a defining a plurality of rows rising diagonally from bottom left to top right along dashed-dotted lines 15a and a series of compressed debosses 70b defining a plurality of rows rising diagonally from bottom right to top left along dashed-dotted lines 15b. The dashed-dotted lines 15a extending through central regions of the respective compressed debosses 70a diagonally intersect with the dashed-dotted lines 15b and with the crests 61 and the troughs 62. Of intersection angles between the dashed-dotted lines 15a and the dashed-dotted lines 15b, an intersection angle alpha opening in the longitudinal direction A is equal to or larger than an intersection angle beta opening in the transverse direction B and preferably in a range of 90 to 150°. While the compressed debosses 70 are formed in the crests 61 as well as in the troughs 62 and the respective crests 61, the preferred crests 61 include the compressed debosses 70a and/or the compressed debosses 70b formed in apexes 61a (See FIGS. 6 and 7) thereof also. In the illustrated embodiment, the dashed-dotted lines 15a intersect with the dashed-dotted lines 15b at the respective apexes 61a and the compressed debosses 70a and the compressed debosses 70b overlap together at the respective apexes 61a. On the topsheet 11, an area surrounded by each pair of the adjacent dashed-dotted lines 15a and each pair of the adjacent dashed-dotted lines 15b has a parallelogram shape and serves as each of skin-contactable areas 75 in the topsheet 11. The preferred skin-contactable area 75 includes at least one crest 61 along which this area 75 may be put in contact with the wearer's skin. The compressed debosses 70a, 70b may have an appropriate planar shape selected from various shapes such as circular shape, oval shape, rectangular shape and rhombic shape and its area is preferably in a range of 0.2 to 9 mm². A center-to-center distance of the adjacent compressed debosses 70a as well as a center-to-center distance of the adjacent compressed debosses 70b, in any case, is preferably set so that such center-to-center distance should not exceed an apex-to-apex distance of the adjacent crests 61 and the crests 61 may be formed at the apexes 61a thereof with the compressed debosses 70a and/or the compressed debosses 70b. A distance 76a between each pair of the adjacent dashed-dotted lines 15a as well as a distance 76b between each pair of the adjacent dashed-dotted lines 15b is preferably adjusted so that at least one row of the crests 61 may be present within each of the skin-contactable areas 75.

The topsheet 11 formed with the skin-contactable regions 75 can rapidly wipe-off bodily fluids such as urine attached to the wearer's skin under the effect of the crests 61 in the respective skin-contactable regions 75 and the compressed debosses 70a, 70b included in these crests 61. The wipe-off properties of the topsheet 11 can be represented by "wipe-off efficiency" to be described later and this "wipe-off efficiency" of the topsheet 11 as one example of the liquid-pervious sheet according to this invention is 95% or higher.

FIG. 5(a) is a sectional view of the topsheet 11 alone taken along line V-V in FIG. 4 and FIG. 5(b) is a partially scale-enlarged diagram of FIG. 5(a). Referring to FIG. 5(a), the compressed debosses 70 are formed on the apices 61a of the crests 61 and thereby each crest 61 is divided into two lower crests 61d. The skin-contactable area 75a is formed between a pair of the compressed debosses 70 and this skin-contactable area 75a includes the crest 61 and the apex 61a both being formed with none of the compressed debosses 70. On the immediate right side of the skin-contactable area 75a, a skin-contactable area 75b having the same cross-sectional shape as that of the skin-contactable area 75a is formed.

In FIG. 5(b), the staple fibers 112 forming the topsheet gather together without losing the individual fiber configuration more densely in the compressed debosses 70 than in the areas 77 surrounding the respective compressed debosses 70 so that the individual staple fibers 11 can be visually confirmed. Consequentially, bodily fluids having been absorbed by the crests 61d in FIG. 5(a) smoothly moves from the surrounding areas 77 toward the compressed debosses 70 and can be quickly absorbed by the core 13 (See FIG. 2). The condition in which the staple fibers 112 densely gather together in the compressed debosses 70 can be confirmed by observing the compressed debosses 70 and the vicinity thereof from above using an electronic microscope at an appropriate magnification (See FIG. 7).

In FIG. 6, the core 13 is not shown for convenience of illustration. The crest 61 in the skin-contactable area 75a is formed, at both ends thereof as viewed in the longitudinal direction A, with the debosses 70a and the debosses 70b, respectively. The skin-contactable area 75a is formed, on both sides thereof as viewed in the longitudinal direction A thereof, with a skin-contactable area 75c, 75d respectively include relatively low crests 61e, 61f (See FIG. 4 also). In the debosses 70a, 70b in FIG. 6 also, the staple fibers 112 gather together more densely than in the surrounding areas. Consequently, when bodily fluids, once having been absorbed by the crest 61, the crest 61e and the crest 61f, disperse in the longitudinal direction A, bodily fluids move toward the debosses 70a, 70b and are absorbed by the core 13 via these debosses 70a, 70b.

Figure 7:
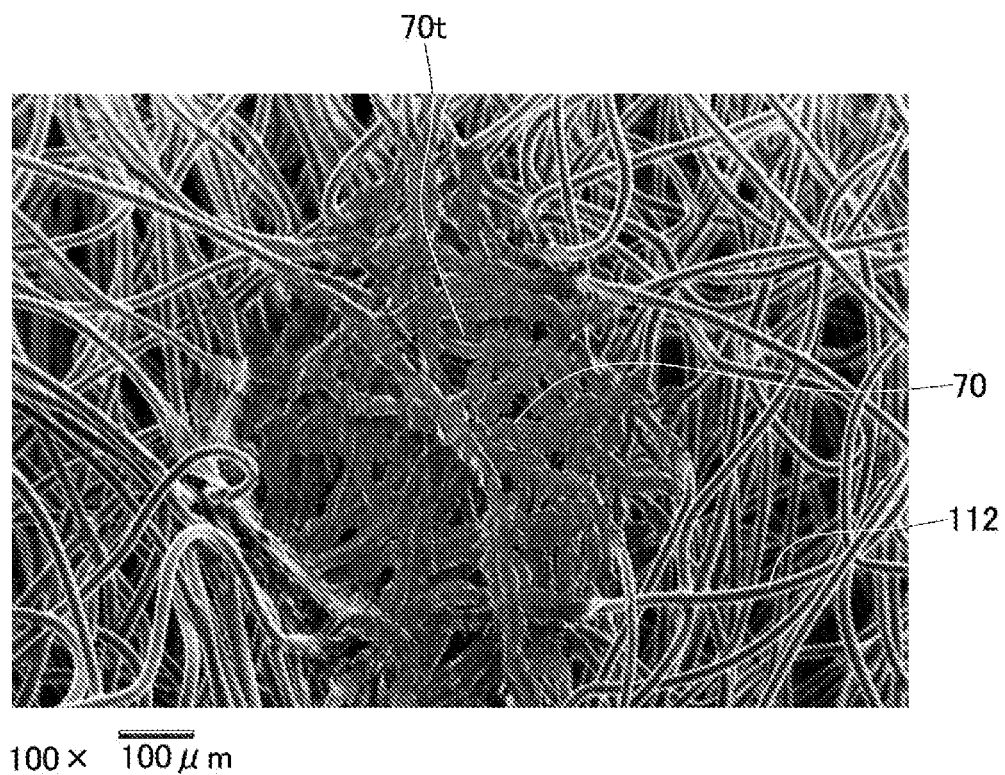
FIG. 7
A magnified photo of compressed debosses.

A photo in FIG. 7 is that used to observe the compressed debosses 70 formed in the liquid-pervious sheet according to Inventive Example 1 to be described later from above at magnification of ×100. In the respective compressed debosses 70, the staple fibers 112 gather together leaving fiber interstices 70t. While each of the staple fibers 112 initially having a substantially circular cross-sectional shape seems to be flattened, the individual staple fibers 112 still maintain their fiber configuration. For this observation of the compressed debosses 70, Real Surface View Microscope VE-7800 manufactured by Keyence Corporation was used.

Figure 8:
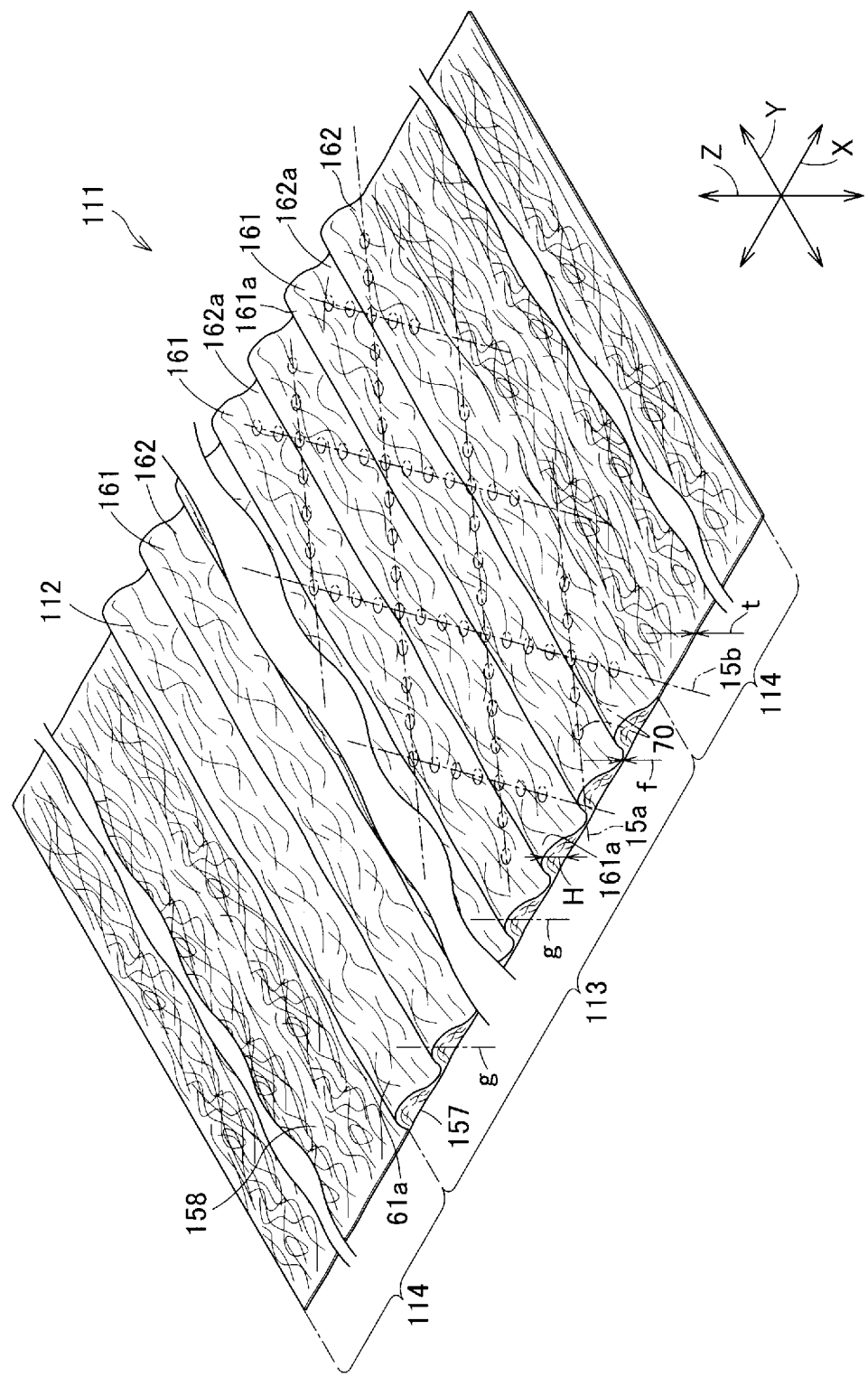
FIG. 8
A partially cutaway perspective view showing a sheet material for the topsheet of the diaper of FIG. 1.

FIG. 8 is a partially cutaway perspective view of a sheet material 111 for the topsheet 11 wherein the dashed-dotted lines 15a, 15b in FIG. 4 and positions of the compressed debosses 70 in a portion of the sheet material 111 are indicated by imaginary lines. The sheet material 111 is nonwoven fabric formed of staple fibers 112 interlaced and fusion bonded together wherein each of the staple fibers has fineness in a range of 1 to 4 dtex and has been treated to become hydrophilic. The sheet material 111 has an upper surface 158 and a lower surface 157 and a basis mass in a range of about 10 to about 50 g/m². The staple fibers 112 may have substantially the same fiber length or may have uneven fiber lengths so far as the fiber length is in a range of about 30 to about 60 mm. Furthermore, the staple fibers 112 may be ones remaining straight or ones crimped by a mechanical or thermal treatment. In the crimped staple fibers 112, values obtained by measurement conducted on the crimped staple fibers after they have been straightened are recorded as the fiber length thereof. The thermoplastic synthetic resin forming the staple fibers 112 may be appropriately selected from a group including polyethylene, polypropylene, nylon and polyester. It is also possible to use a so-called core-in-sheath type or side-by-side type conjugate fibers composed of at least two types of the above-mentioned thermoplastic synthetic resin as the staple fibers 112. The sheet material 111 is formed in a central zone thereof as viewed in a first direction X corresponding to the transverse direction B of the diaper 1 in FIG. 1 is formed with an undulating zone 113 and on both sides of the undulating zone 113 with flat zones 114. The undulating zone 113 is formed on its upper surface 158 with crests 161 and troughs 162 alternate in the first direction X and a distance between the respective apexes 161a of the adjacent crests 161 as well as a distance between respective bottoms 162a of the adjacent troughs 162 is in a range of about 2 to about 7 mm. These crests 161 and troughs 162 extend in parallel to one another in a second direction Y corresponding to the longitudinal direction A of the diaper 1. A dimension H from the lower surface 157 to an apex 161a of the crest 161 measured in a third direction Z extending orthogonally to the first direction X and the second direction Y defines a height of the crest 161 (See FIG. 2). In description of the present invention, the dimension H is sometimes designated as a thickness of the sheet material 111 in the undulating zone 113 or a thickness of the sheet material 111 under no load and the third direction Z is sometimes designated as a thickness direction of the sheet material 111. A dimension between the upper surface 158 and the lower surface 157 in the trough 162 is denoted by f. The flat zone 114 has the same mass per unit area as that of the undulating zone 113 and a dimension between the upper surface 158 and the lower surface 157 of the undulating zone 113 is denoted by t (See FIG. 2). In the preferred sheet material 111, the dimension H is in a range of about 0.6 to about 2.5 mm, the dimension f is in a range of about 0.4 to about 0.6 mm and the dimension t is in a range of about 0.2 to about 0.7 mm.

Assuming that such sheet material 111 is formed with the compressed debosses 70 exemplarily illustrated in FIGS. 4 through 6 and then cut into a predetermined dimension to be used as the topsheet 11 as illustrated in FIGS. 1 through 3, the upper surface 158 and the lower surface 157 of the sheet material 111 define the upper surface and the lower surface 57 of the topsheet 11, respectively. The undulating zone 113 and the flat zone 114 of the sheet material 111 define the central zone 60a and the lateral zones 60b of the topsheet 11, respectively, and the crests 161 and the troughs 162 of the sheet material 111 define the crests 61 and the troughs 62 of the topsheet 11, respectively.

Figure 9:
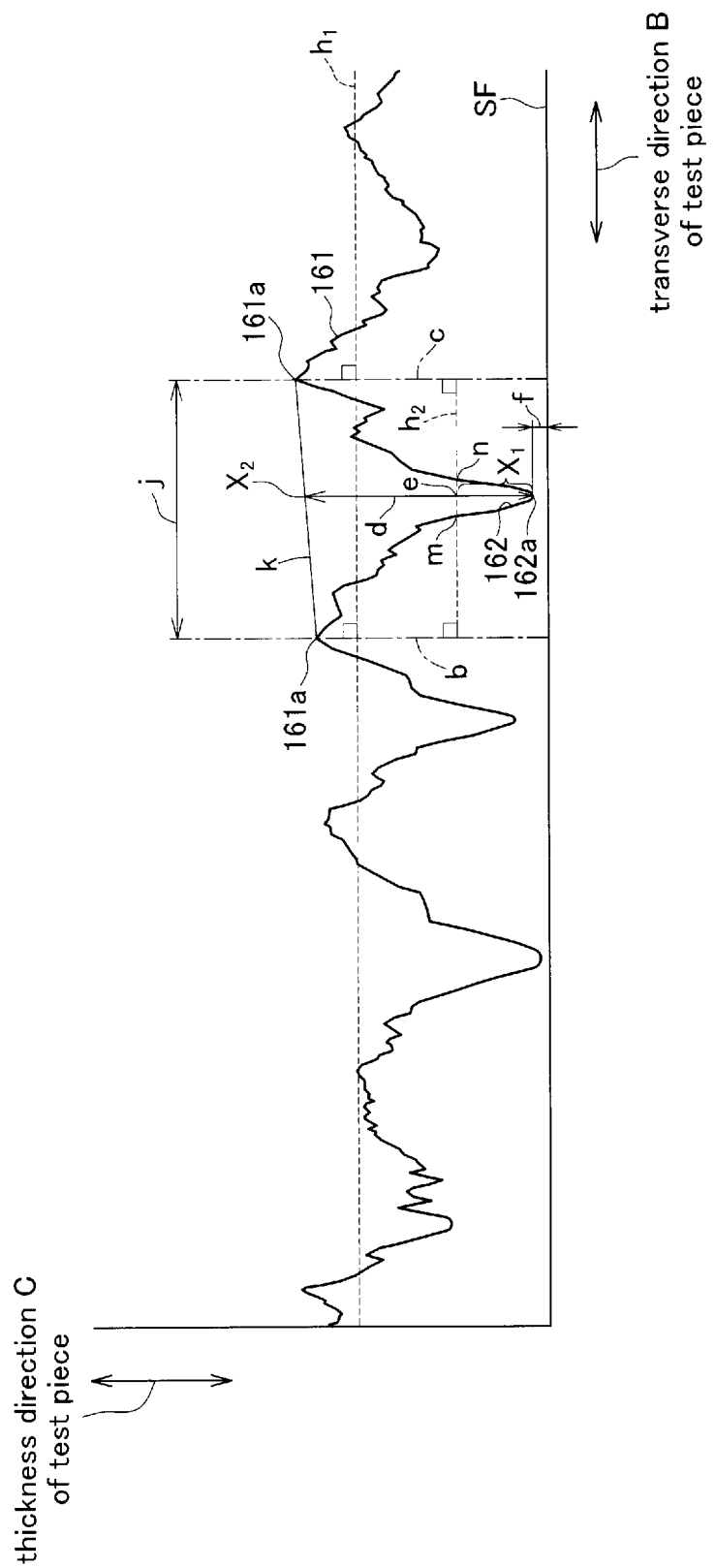
FIG. 9
A sectional view used to measure a dimension of liquid-pervious sheet.

FIG. 9 is a diagram illustrating a procedure for measurement of dimensions H, f, t and others. For measurement, test pieces for measurement are prepared from the sheet material 111 of the topsheet 11. The test pieces are cut from the sheet material 111 or the topsheet 11 and respectively have a length of at least 30 mm in the first direction X or the transverse direction B.

Each of the test pieces is placed on a horizontal plane with the crests 161 or 61 with the crests 161 or 61 facing upward and, as a three dimensional measuring machine, High Accuracy Geometry Measuring System (including High Accuracy Stage: KS-1100) and High-Speed High-Accuracy CCD-Laser Displacement Gauge (including Controller: LK-G3000V Set, and Sensor Head: LK-G30) are used and setting conditions of these instruments are set to measure a cross-sectional shape of the respective test pieces and to record them.

Conditions for Instrument Setting

| Stage: KS-1100 | |
| --- | --- |
| 1. Measurement range | 30000 micrometers × 30000 micrometers |
| 2. Measurement pitch | 20 micrometers |
| 3. Movement rate | 7500 micrometers/second |
| 1. Measurement mode | measuring object |
| 2. Installation mode | diffused reflex |
| 3. Filtering | 4 times on average |
| 4. Sampling period | 200 microseconds |

Controller: LK-G30000V Set

To obtain a profile line of the cross-sectional shape subjected to a smoothing processing, a graphic data processing is carried out under the conditions as follows.

1. File of measurement date is opened up.
2. "Profile" is selected and then a horizontal line is selected.
3. A location to be measured is selected so that any one of the compressed debosses in the test piece should not be included.
4. "Adjustment" is selected, then "Height smoothing" is selected and finally "+ or −12" is selected.

From the profile line having been subjected to the smoothing processing, various dimensions are determined by the following steps as follows. Details of the steps will be described below in reference to FIG. 9. It should be noted that the profile line having been subjected to the smoothing processing is indicated in FIG. 9.

1. An auxiliary line k connecting the adjacent crests 161 on the profile line is drawn.
2. A first horizontal line $h_1$ extending in parallel to the horizontal plane SF is drawn.
3. Auxiliary lines b, c extending through the respective apexes 161a and being orthogonal to the first horizontal line $h_1$ are drawn.
4. An auxiliary line d extending through the bottom 162a of the trough 162 and being orthogonal to the first horizontal line $h_1$ is drawn.
5. An intersecting point of the auxiliary line k and the auxiliary line d is denoted by $X_2$.
6. On the auxiliary line d, a point e at a distance from the bottom 162a corresponding to ⅓ of a distance from the bottom 162a to the intersecting point $X_2$. A distance from the bottom to the point e is denoted by $X_1$.
7. A second horizontal line $h_2$ extending through the point e in parallel to the first horizontal line $h_1$ is drawn, then intersecting points m, n between the second horizontal line $h_2$ and the profile line segment connecting the adjacent crests 161 are obtained and a distance between the point m and the point n is determined as a width dimension of the associated trough 162.
8. A distance between the auxiliary line c and the auxiliary line d is determined as a distance between the adjacent apexes 161a or as a pitch between the adjacent crests 161.
9. A difference between the apex-to-apex distance and the width dimension of the associated trough is determined as the width dimension of the associated crest 161.
10. With respect to the auxiliary lines b, c, a distance from the horizontal plane SF to the apexes 161a, namely, a dimension H is determined as a height of the associated crests under no load or a thickness dimension of the sheet material 111 or the topsheet 11 under no load.
11. Along the auxiliary line d, a distance from the bottom 162a to the horizontal plane SF is determined as the dimension f of the respective test pieces.
12. When the test piece includes the flat portion 114 of the sheet material 111, the steps as have described above may be applied to such flat portion 114 also to determine the dimension f for the flat portion 114.
13. The respective dimensions of the sheet materials 111 and/or the topsheet 11 are measured once for each test piece and average of values obtained from total 10 measurements for 10 test pieces.

In the chassis 2 of the diaper 1 exemplarily illustrated in FIG. 1, the backsheet 12 is formed from a film of thermoplastic synthetic resin such as polyethylene having a thickness in a range of 0.01 to 0.05 mm and the outer sheet 14 is formed of nonwoven fabric having a basis mass in a range of 10 to 40 g/m$^2$, for example, a spunbond nonwoven fabric, an SMS (spunbond-meltblown-spunbond) nonwoven fabric or a spunlaced nonwoven fabric. The containment flap 31 is formed of a poorly liquid-pervious, more preferably, liquid-impervious nonwoven fabric or a film of thermoplastic synthetic resin. The front wings 3 and the rear wings 4 are formed of a nonwoven fabric or a laminate composed of a nonwoven fabric and a film of thermoplastic synthetic resin.

Figure 10:
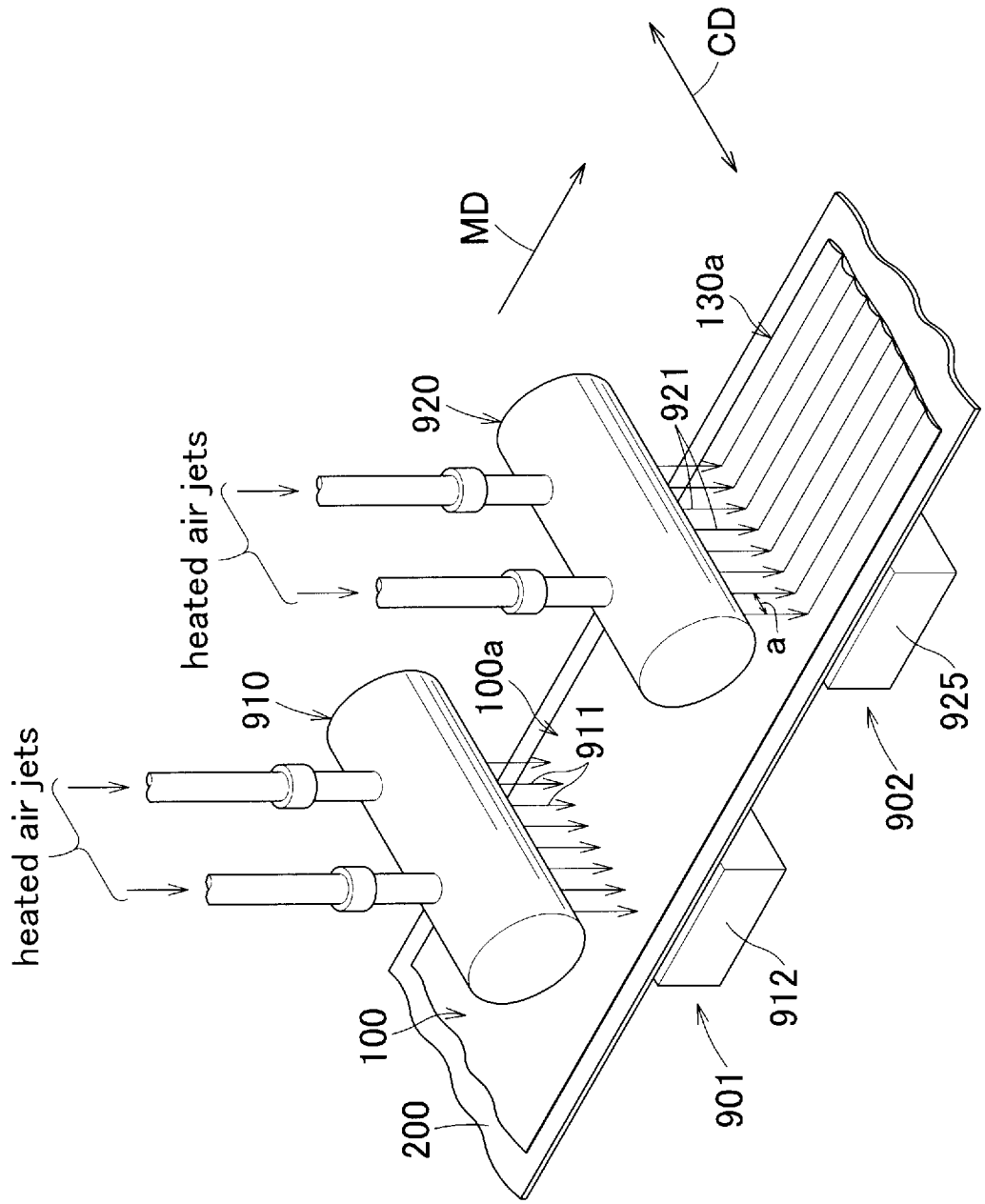
FIG. 10
A diagram illustrating a part of the manufacturing process for the liquid-pervious sheet.
Figure 11:
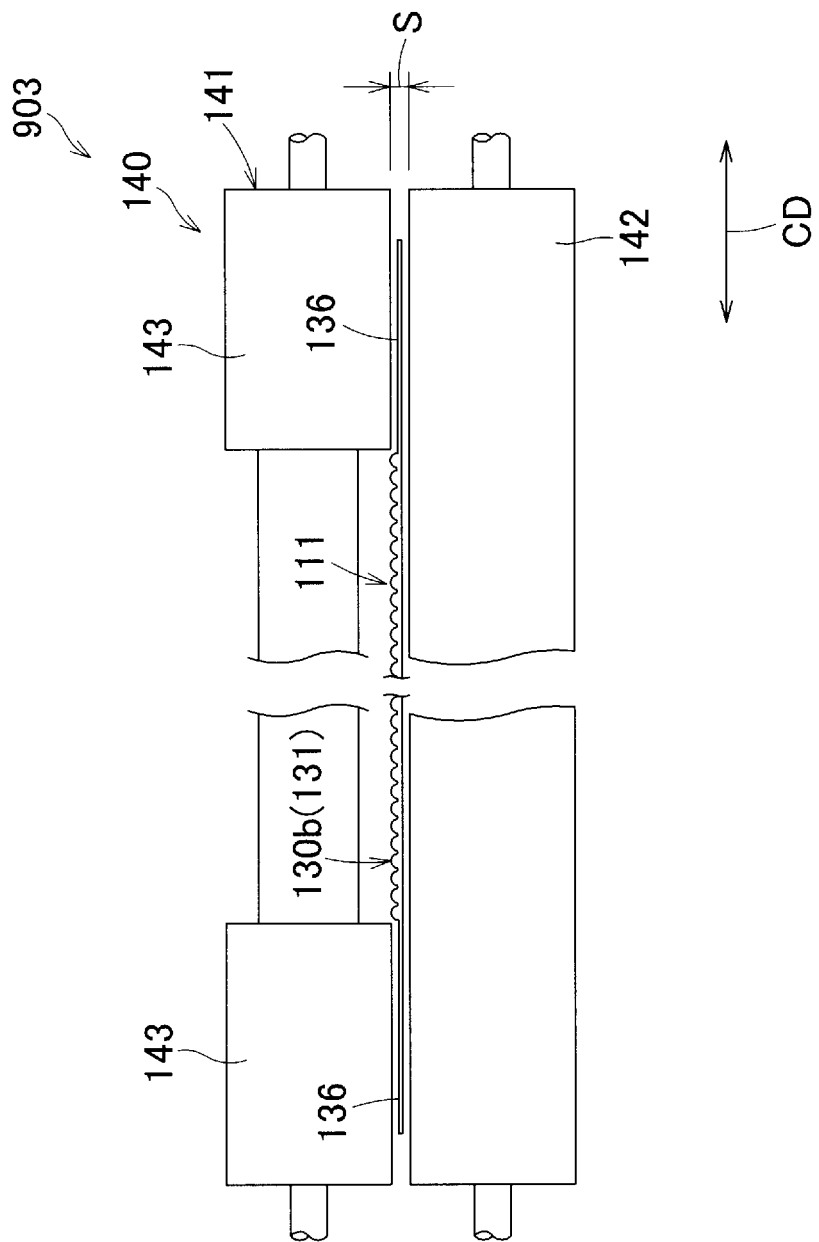
FIG. 11
A diagram illustrating a part of the manufacturing process for the liquid-pervious sheet.

FIG. 10 is a diagram partially illustrating a step of making first nonwoven fabric 130a to be used as the sheet material 111 shown in FIG. 8 from carded web 100 and FIG. 11 is a diagram partially illustrating a step of obtaining a web 131 of the sheet materials 111 from the first nonwoven fabric 130a wherein the step illustrated in FIG. 10 is well known from JP 2009-030318 A.

Referring to FIG. 10, a carded web 100 formed of the staple fibers 112 and having a basis mass in a range of about 10 to about 50 g/m$^2$ is loaded on a conveyor belt 200 which is air-permeable in its thickness direction and conveyed in a machine direction MD. The conveyor belt 200 may be formed, for example, of a mesh plate of 30 meshes or more. In the order as viewed in the machine direction MD, the method of making the liquid-pervious sheet according to the present invention includes a first step 901 as a step of primary treatment in which the staple fibers 112 (See FIG. 3) are fusion bonded together while the carded web 100 is compressed in its thickness direction in order to stabilize a formation of the carded web and a second step 902 in which the carded web 100 having been preliminarily treated in the first step 901 is formed with crests 161 and troughs 162. In the first step 901, the carded web 100 is blasted with first heated jet air streams 911 from a first nozzle array 910. The first jet air streams 911 flows through the carded web 100 and the belt 200 and is sucked by a first suction box 912. An air volume of the first jet air is set to a value equal to or slightly more than an air-intake volume per unit time of the first suction box 912 so that the preliminary treatment may be reliably achieved. A temperature of the first jet air streams 911 is set a temperature at which the surfaces of the staple fibers 112 may be slightly molten and the staple fibers 112 may be fusion bonded together merely on mutual contact surfaces thereof without a possibility that the staple fibers 112 might lose initial fibrous configuration.

In the second step 902, the carded web 100a having been preliminarily treated in the step 1 is blasted with a series of heated second jet air streams 921 from a second nozzle array 920 including a series of nozzles (not shown) arranged at a center-to-center spacing a in a cross direction CD and thereby a first nonwoven fabric 130a is obtained. The staple fibers 112 in the carded web 100a preliminarily treated in the step 1 so as to have the fibrous formation thereof are now partially displaced in the cross direction CD by the second jet air streams 921 so that the crest 161 may be formed between each pair of the adjacent second jet air streams 921. An air volume of the second nozzle array 920 is preferably set to a value larger than an air-intake volume of a second suction box 925. Positions of the second jet airstreams 921 blasted from the second jet array 920 arranged at the center-to-center spacing a in the cross direction CD correspond to the positions of the troughs 162 on the sheet material illustrated in FIG. 8. In the first nonwoven fabric 130a, the staple fibers 112 lying just below the second jet air streams 921 are partially displaced so as to be parted equally on both sides of the cross direction CD and to participate formation of the crests 161 and the staple fibers 112 remaining just below the second jet air streams 921 form the troughs 162. Such second jet airstreams 921 serves also to orient the staple fibers 112 in the machine direction MD. Though not illustrated, the second step may include a heat treatment chamber at the downstream of the second nozzle array 920. The heat treatment chamber may function to heat the first nonwoven fabric 130a so that the surfaces of the staple fibers 112 may be slightly molten and the number of regions in which the staple fibers 112 are fusion bonded may be increased to stabilize the fibrous formation of the first nonwoven fabric 130a.

In a third step schematically illustrated in FIG. 11, second nonwoven fabric 130b cut from the first nonwoven fabric 130a so as to have an appropriate width dimension is pressurized under heating by a press roll 140 to obtain the web 131 of the sheet materials 111. The press roll 140 comprises an upper roll 141 and a lower roll 142 both rotating in the machine direction MD. The upper roll 141 includes a pair of diameter-enlarged segments 143 on ends opposite in the cross direction CD and these diameter-enlarged segments 143 maintained at a predetermined temperature. The lower roll 142 serves to support the second nonwoven fabric 130b from below as viewed in FIG. 11. The diameter-enlarged segments 143 of the upper roll 141 cooperate with the lower roll 142 to compress opposite lateral zones 136 of the second nonwoven fabric 130b as viewed in the cross direction CD under heating. It should be noted that it is possible to heat the lower roll 142 at a predetermined temperature during use thereof and it is also possible to use the lower roll 142 without heating this. A clearance S between the diameter-enlarged segments 143 and the lower roll 142 may be adjusted so that the opposite lateral zones 136 of the second nonwoven fabric 130b can be compressed to a desired thickness. In a similar fashion, a circumferential velocity of the diameter-enlarged segments 143 and the lower roll 142 may be adjusted so that a compression time required to compress the opposite lateral zones 136 to the desired thickness can be assured. The diameter-enlarged segments 143 set to a temperature 3 to 20° C. lower than a fusion temperature of thermoplastic synthetic resin forming the staple fibers 112 may be used to compress the second nonwoven fabric 130b under heating and then rapidly cooled to room temperature to maintain the staple fibers in the state deformed under compression, on one hand, and to deform the opposite lateral zones 136 from the undulated zones including the crests 161 to the flat zones 114 (See FIG. 3) having a small thickness t (See FIG. 2), on the other hand. The second nonwoven fabric 130b including the lateral zones 136 deformed in this manner is the web of the sheet materials Generally in the sheet material 111, density is apt to be higher in one of the crest 161 and the trough 162 than in the other of the crest 161 and the trough 162 depending on characteristics of the carded web 100 used to make the sheet material 111, operating conditions of the first and second steps 901, 902 in FIG. 10 and the other factors. For example, the staple fibers 112 are apt to be closer to one another than in the crests 161, i.e., to have a density higher than in the crests 161. The staple fibers 112 in the crests 161 are apt to extend in parallel to one another in the machine direction MD.

In the third step 903 illustrated in FIG. 11, blowers serving to cool the opposite lateral zones 136 of the web 131 may be provided on the downstream of the roll 140. An additional roll similar to the roll 140 may be located on the downstream of the roll 140 to assure a sufficient time to pressurize the opposite lateral zones 136 under heating.

Figure 12:
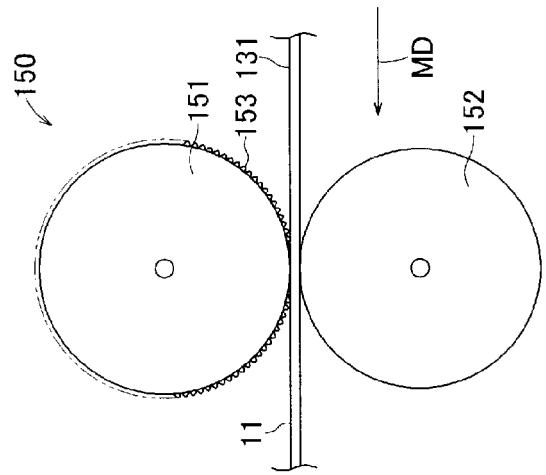
FIG. 12
A diagram illustrating a part of the manufacturing process for the liquid-pervious sheet.

FIG. 12 is a diagram schematically illustrating a step of forming the web 131 of the sheet materials 111 obtained in the second step illustrated in FIG. 11 with the compressed debosses 70. In the step of FIG. 12, the web 131 obtained in the step of FIG. 11 is continuously fed in the machine direction MD to a debossing calender 150 including an upper roll 151 and a lower roll 152. The upper roll 151 is formed on its peripheral surface with a series of bosses 153 in the same distribution pattern as the distribution pattern of the compressed debosses 70 exemplarily illustrated in FIG. 4 and the lower roll 152 has a smooth peripheral surface. Both the upper roll 151 and the lower roll 152 are temperature adjustable. Specifically, a temperature of the bosses 153 of the upper roll 151 and a surface temperature of the lower roll 152 are heated at the most to a temperature at which the staple fibers 112 of thermoplastic synthetic fibers constituting the web 131 can be softened but not heated to a temperature at which the staple fibers 112 are molten. In the debossing calender 150, nose geometry, length and surface pressure of the boss 153 may be adjusted to select depth and shape of the compressed deboss 70 formed on the web 131. The temperature of the bosses 153 may be set to the softening temperature of the staple fibers 112 to assure that the staple fibers 112 lying in the compressed debosses 70 and directly underlying the compressed debosses can more densely gather together than in the surrounding zones and, in addition, to assure that the staple fibers 112 lying in the compressed debosses 70 and directly underlying the compressed debosses can maintain the fibrous formation of the staple fibers 112 (See FIG. 5).

When the web 131 having been embossed in the step illustrated in FIG. 12 is used as the topsheet 11, bodily fluids absorbed first by the topsheet 11 in the compressed debosses 70 smoothly move from the surrounding zone in which the staple fibers 112 are distributed at a relatively low density to the compressed debosses 70 in which the staple fibers 112 are densely gathered together. In consequence, the surface of the topsheet 11, particularly the apexes 61a of the crests 61 and the vicinity thereof can rapidly recover the desired dry condition. With such topsheet 11, an uncomfortable feeling of wetness inevitably experienced by the wearer should not last long period and consequently the feeling of wetness is negligible. So-called Q-max value to be described later of the topsheet 11 having such function does not exceed 0.10 kw/m$^2$. The topsheet having the Q-max value exceeding 0.10 kw/m$^2$ will be disadvantageous in that a noticeable amount of moisture may stay on its surface and the wearer may experience an uncomfortable feeling of coldness upon contact of the wearer's skin with the topsheet and sometimes such moisture may cause any skin trouble such as rash.

In the debossing calender 150, a height of each boss 153 may be set to be sufficiently short to assure that the peripheral surface of the upper roll 151 can effectively pressurize the surface of the web 131. In such upper roll 151, the bosses 153 advantageously facilitate these bosses 153 to be kept at a desired temperature. In addition, the peripheral surface of the upper roll 151 can pressurizes the web 131 to a desired thickness. However, when the web 131 is excessively thinned by the debossing calendar 151, a desired soft texture of the web 131 should be lost and eventually its cushioning properties should be deteriorated. To avoid such problem, the thickness of the topsheet 11 in the central zone 60a thereof (See FIG. 2) is preferably 60% or higher of the thickness of the first nonwoven fabric 130a in FIG. 8. Such topsheet 11 may have a softer texture than that of the sheet material used as the standard sheet material in the paragraph "softness of texture" to be described later. While the surface figure as well as the side geometry of the web 131 changes between before and after passage through the debossing calender 150, such change in the surface figure as well as the side geometry is not shown in FIG. 12 for convenience of illustration.

Figure 13:
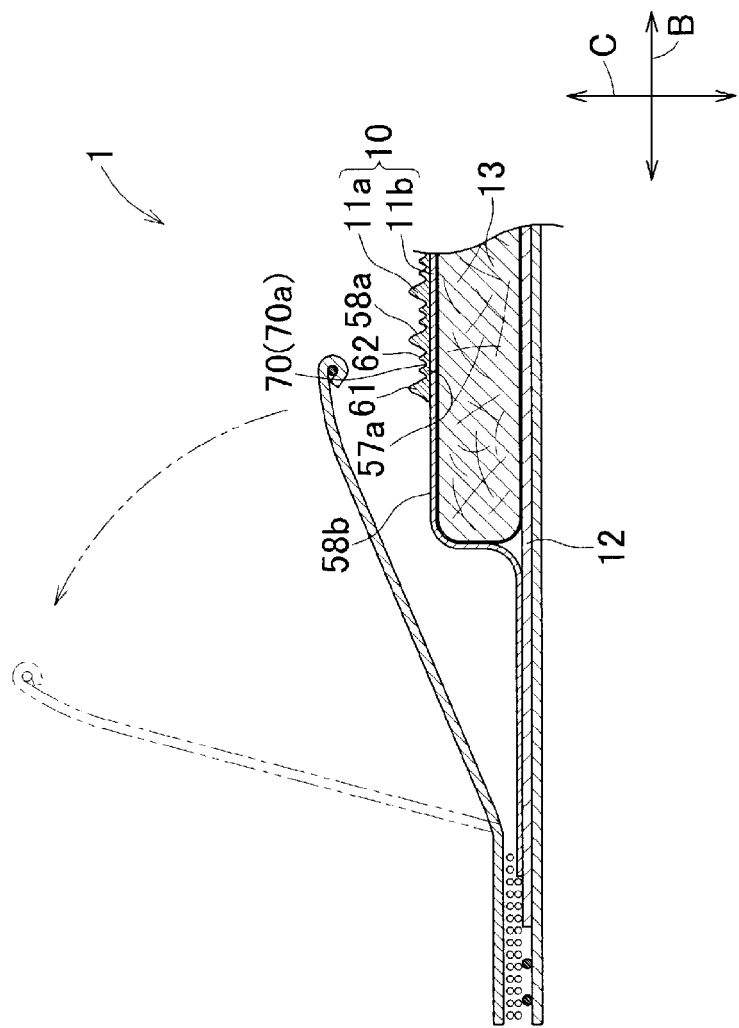
FIG. 13
A view similar to FIG. 2, showing one embodiment.

FIG. 13 is a view similar to FIG. 2, exemplarily illustrating one embodiment of this invention. In the diaper 1 illustrated in FIG. 13, the liquid-pervious topsheet 11 is formed from a liquid-pervious composite sheet 10. The composite sheet 10 composed of a liquid-pervious first topsheet 11a and a liquid-pervious second topsheet 11b bonded together with hot melt adhesive (not shown) wherein an upper surface 58b of the second topsheet 11b is bonded to a lower surface 57a of the first 11a. The first topsheet 11a is similar to the topsheet 11 exemplarily illustrated in FIGS. 4 through 6. Specifically, the topsheet 11a is formed of the staple fibers 112 and formed on its upper surface 58a with the crests 61, the troughs 62 and the compressed debosses 70a, 70b and has its lower surface 57a formed flat. A height of each crest 61 in the first topsheet 11a may be dimensioned to be the same as or lower than the height H of each crest 61 in FIG. 2. Similarly, the dimension of the first topsheet 11a in the longitudinal direction A may be set to be the same as or shorter than that of the second topsheet 11b in the topsheet 11. The dimension (width) of the first topsheet 11a in the transverse direction X also may be set to be the same as or smaller than the dimension in the transverse direction B (width) of the central zone 60a of the topsheets 11 in FIG. 2.

The second topsheet 11b in FIG. 13 may be formed from a nonwoven fabric of hydrophilized thermoplastic synthetic fibers 110 (See FIG. 14) such as a spunbond nonwoven fabric, a spunlaced nonwoven fabric or an SMS nonwoven fabric (a laminate of spunbond nonwoven fabric, a meltblown nonwoven fabric and a spunbond nonwoven fabric). For the nonwoven fabric as has been described above, staple fibers and/or filaments each having fineness in a range of about 1 to about 4 dtex and a basis mass in a range of about 10 to about 50 g/m$^2$ may be used as component fibers. As the staple fibers and filaments, core-in-sheath type conjugate fibers or side-by-side type conjugate fibers also may be used. Such second topsheet 11b covers the upper surface of the core 13 and extends outward beyond the peripheral edge of the core 13 in the longitudinal direction A and in the transverse direction B so as to overlap the backsheet 12 and bonded thereto with hot melt adhesive (not shown).

In the diaper 1 illustrated in FIG. 13 using the composite sheet 10 in the place of the liquid-pervious topsheet 11, the first topsheet 11a having a size smaller than the topsheet 11 used in the embodiment illustrated in FIG. 1 may be used in consideration that the first topsheet 11a is apt to increase a manufacturing cost and the core 13 may be covered with the second topsheet 11b adapted to keep the manufacturing cost for the diaper 1 low.

Figure 14:
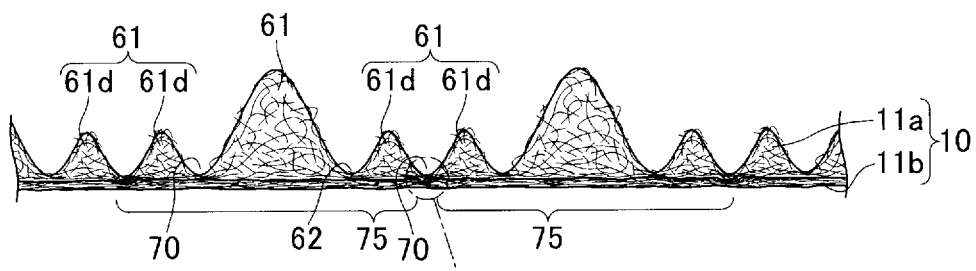
FIG. 14
A view similar to FIG. 4, showing one embodiment.
Figure 14:
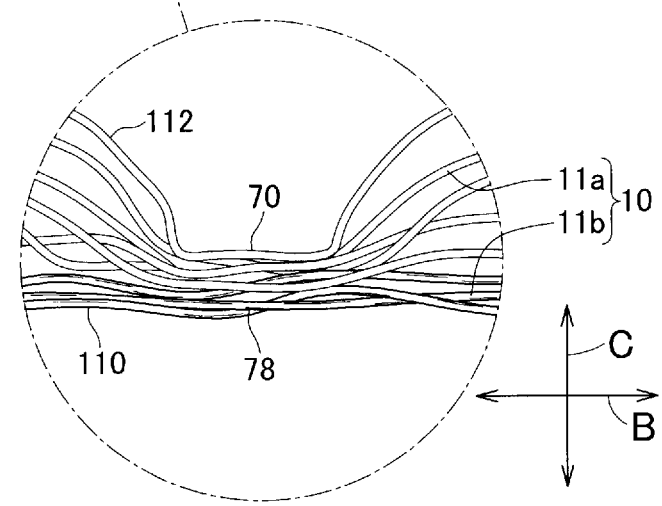
Figure 15:
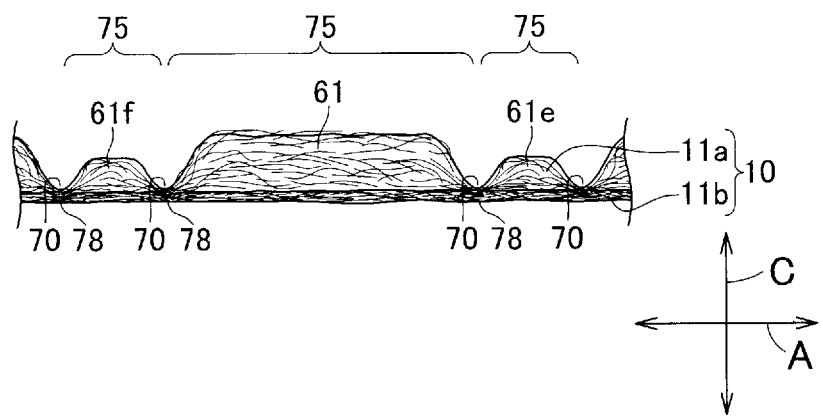
FIG. 15
A view similar to FIG. 5, showing one embodiment.

FIGS. 14 and 15 are views similar to FIGS. 5 and 6, illustrating the composite sheet 10 of FIG. 13. FIG. 14(a) exemplarily shows a sectional view of the composite sheet 10 taken in the transverse direction B wherein the composite sheet 10 includes the first topsheet 11a and the second topsheet 11b. In the compressed deboss 70 illustrated in FIG. 14(b), the staple fibers 112 in the first topsheet 11a densely gather together compared to the staple fibers 112 in the compressed deboss surrounding area. In the second topsheet 11b, the area 78 aligned with the compressed deboss 70 in the thickness direction C, in other words, the area 78 directly underlying the compressed deboss 70 contains the thermoplastic synthetic fibers 110 forming the second topsheet 11b gather together at a density higher than in the area surrounding the area 78 and defines a second compressed deboss 78. The composite sheet 10 is formed with skin-contactable areas 75.

The composite sheet 10 in FIG. 13 is also formed with the crests 61, 61e, 61f and the skin-contactable areas 75 similar to those illustrated in FIG. 6. The first topsheet 11a is formed with the compressed debosses 70 and the second topsheet 11b is formed with the second debosses 78.

The composite sheet 10 exemplarily illustrated in FIGS. 13 through 15 may be made by the following steps as will be described below. The nonwoven fabric having been hydrophilized to be used as the second topsheet 11b is bonded to the flat lower surface of the first nonwoven fabric obtained in the step of FIG. 10 with hot melt adhesive to obtain a precursor of the composite sheet 10. The precursor is fed to the debossing calender 150 illustrated in FIG. 12 wherein the first nonwoven fabric 130a is embossed by the bosses 153 of the upper roll 151. Height of these bosses 153 may be appropriately selected considering the thickness of the precursor and the depth of the compressed debosses 70 to be formed in the precursor.

EMBODIMENTS

As embodiments according to this invention, the liquid-pervious sheets corresponding to the composite sheets exemplarily illustrated in FIGS. 13 through 15 were made and respective data of Q-max value, remaining quantity for artificial urine, wipe-off efficiency for artificial urine, softness of texture and thickness of the first topsheet were measured and evaluated. The respective data were evaluated in the manners as follows.

1. Q-Max Value, Remaining Quantity, Wiping-Off Efficiency (1) Q-max value is defined by a quantified value of heat drawn by the topsheet wetted with bodily fluids from the wearer's skin when the wearer's skin comes in contact with such topsheet and this value is thought to be in proportional relation with a quantity of moisture on the surface of the topsheet. Specifically, the higher the Q-max value is, the larger a quantity of moisture on the surface of the topsheet and correspondingly the larger the quantity of heat drawn from the wearer's skin is. In such situation, the wearer's skin will experience chill all at once. For measurement of the Q-max value, KES-F7-THERMOLABO II Model high-accuracy & high-speed thermal property measuring device manufactured by KATO TECH CO. LTD. was used.

(2) A plurality of the first topsheets and the second topsheets each having a size of 100×100 mm were prepared as the inventive examples and the comparative examples, respectively, and each of these sheets was placed on a central zone of the absorbent structure on its side facing the wearer's skin. The absorbent structures were detached from the commercially available disposable diapers (Moony S-size of Unicharm Corporation) to obtain test pieces to measure Q-max values of the liquid-pervious sheets according to the Inventive Examples and the Comparative Examples.

(3) As an equivalent to the wearer's skin, artificial leather of 100×100 mm ("Supplare" PZ12002 (color C/black) manufactured by Idemitsu Technofine Co., Ltd.) was prepared and its mass A was determined. 1.0 ml of artificial urine was dropped onto this artificial leather until artificial urine dropped in this manner spread to make a circle having a diameter of 40 mm whereupon a total mass B of the artificial leather plus the artificial urine was determined. To prepare the artificial urine, dissolved in ion-exchanged water were urea in 2%, sodium chloride in 0.8%, magnesium sulfate hydrate in 0.08% and calcium chloride dihydrate in 0.03% on the basis of the mass of ion-exchanged water, and a temperature thereof is adjusted at 20° C.

(4) A center point on the side of the test piece facing the wearer's skin was aligned with the center of the artificial urine drawing the circle and a weight dimensioned to be 100×100 mm and having a mass of 200 g was placed on the side of the test piece facing away from the wearer's skin.

(5) In contact with the artificial urine, the test piece was reciprocated once leftward by 25 mm and then reciprocated once rightward by 25 mm so as to wipe-off the artificial urine.

(6) In contact with the artificial urine, the test piece was reciprocated once upward by 25 mm and then reciprocated once downward by 25 mm to wipe-off the artificial urine.

(7) The mass C of the artificial leather after the artificial urine had been wiped off was measured to determine a remaining quantity represented by the following formula:

Remaining quantity=mass $C$−mass $A$ and a wipe-off efficiency (%) was calculated from the formula as follows:

Wipe-off efficiency={1−(mass $C$−mass $A$)/(mass $B$−mass $A$)}×100

(8) All operations for measurement were conducted at constant temperature and humidity, specifically, at the temperature of 20° C. and the relative humidity of 65%.

(9) The test piece after the operation of wiping off was left on a desk for 3 minutes with the composite sheet lying above.

(10) During 3 minutes, the test piece was set in the Q-max measuring device placed in a room at a temperature of 20° C. and a relative humidity of 65%.

(11) The temperature control system in KES-F7 includes a pure copper plate (area of 9 cm$^2$, mass of 9.79 g and thermal capacity of 0.41855 J/C.°) and T-Box serving as a heat source adapted to provide the test piece with a temperature difference. The pure copper plate has a precision temperature sensor built in. The temperature of the pure copper plate was set to 30° C. and the pure copperplate was pressed against the test piece set on the measuring device at a load of 10 g/cm$^2$ to read the maximum heat transfer value, i.e., Q-max value (kw/m$^2$). The higher the Q-max value, the larger the quantity of moisture on the surface of the topsheet as the test piece, indicating correspondingly high value of heat transfer. In other words, the lower the Q-max value is, the smaller the quantity of moisture staying on the surface of the topsheet is.

2. Softness of Texture (1) Softness of texture was ranked on the basis of a result of organoleptic test conducted on five trial subjects.

(2) Air-through nonwoven fabric made of core-in-sheath type conjugate fibers composed of polyethylene as sheath and polyester as core was employed as a standard sheet piece serving as criterion of the softness of texture. This air-through nonwoven fabric had fineness of 2.2 dtex, a fiber length of 45 mm, a mass per unit area of 25 g/m$^2$ and a thickness of 0.3 mm. Ranking for respective test pieces was based on judgments of the respective trial subjects when they lightly touched the test pieces and the standard sheet piece. If all of the trial subjects judged that the test piece is softer and kinder to the skin than the standard sheet piece was prevailing, the test piece was ranked as A. If there were mixed judgments that the test piece is softer and kinder to the skin than the standard sheet piece and that the softness of the test piece is similar to that of the standard sheet piece, the test piece was ranked as B. If there were mixed judgments that the softness of the test piece is similar to that of the standard sheet piece and that the test piece is inferior in softness than the standard sheet piece, the test piece was ranked as C. Finally, if all of the trial subjects judged that the test piece is inferior in softness and less kind to the skin than the standard sheet piece was prevailing, the test piece was ranked as D.

(3) To exclude a visual influence from the comparative judgment of the trial subjects, blindfolds were put on the respective trial subjects.

3. Thickness of First and Second Topsheets Under Load (1) As the test pieces, the liquid-pervious sheets according the Inventive Examples and the Comparative Examples each having a size of 100×100 mm were prepared.

(2) When the first topsheets were peeled off from the respective liquid-pervious sheets, the first topsheets were previously subjected to cold spray to cool them and thereby to help prevent the first topsheets from changing in shape and thickness.

(3) As the measuring device, DIAL GAUGE PEACOCK of OZAKI MFG. CO. LTD. was used and a probe having a diameter of 20 mm was used.

The measuring device was previously adjusted so as to have a measuring pressure of 3 g/cm$^2$ to the test pieces. Therefore, values of thickness measured in this manner are the thickness values of the first topsheets or the second topsheets under load.

Inventive Example 1

As the first topsheet in the liquid-pervious sheet according to the Inventive Example 1, the topsheet having characteristics as follows was used.

(1) Construction of the staple fibers
   a. Composition: core-in-sheath type conjugate fibers composed of polyethylene as the sheath and polyester as the core and previously hydrophilized.
   b. Fineness and fiber length: mixture of staple fibers of 50% by mass having fineness of 2.2 dtex, fiber length of 45 mm and staple fibers of 50% by mass having fineness of 3.0 dtex, fiber length of 38 mm
(2) Basis mass: 25 g/m$^2$
(3) Width dimension of crest: 3.2 mm
(4) Width dimension of trough: 0.9 mm
(5) Apex-to-apex distance of adjacent crests: 4.1 mm
(6) Thickness under load: 1.2 mm
(7) Shape, size and center-to-center distance of compressed debosses: A square of 0.7 mm×0.7 mm; center-to-center distance of 1.4 mm
(8) Crossing angle between rows of compressed debosses: α (See FIG. 4)=106°
(9) One side length in each skin-contactable region (See FIG. 4): 9 mm As the second topsheet in the liquid-pervious sheet according to the Inventive Example 1, the topsheet having characteristics as follows was used.
(1) Construction of the staple fibers
   a. Composition: core-in-sheath type conjugate fibers composed of polyethylene as the sheath and polyester as the core and previously hydrophilized.
   b. Fineness and fiber length: mixture of staple fibers of 50% by mass having fineness of 2.8 dtex, fiber length of 38 mm and staple fibers of 50% by mass having fineness of 2.2 dtex, fiber length of 38 mm.
(2) Basis mass: 25 g/m$^2$
(3) Thickness under load: 0.4 mm Inventive Example 2

The liquid-pervious sheet according to Inventive Example 2 was made under the same conditions as those for Inventive Example 1 except that one side length in each of the skin-contactable regions of the first topsheet (See FIG. 4) was changed to 6 mm.

Inventive Example 3

The liquid-pervious sheet according to Inventive Example 3 was made under the same conditions as those for Inventive Example 1 except that one side length in each of the skin-contactable regions of the first topsheet was dimensioned to be 18 mm and a length of respective bosses on the roll 151 of FIG. 12 was dimensioned to be 0.5 mm.

Inventive Example 4

The liquid-pervious sheet according to Inventive Example 4 was made under the same conditions as those for Inventive Example 1 except that one side length in each of the skin-contactable regions of the first topsheet was dimensioned to be 12 mm and a length of respective bosses on the roll 151 of FIG. 12 was dimensioned to be 0.5 mm.

Comparative Example 1

The liquid-pervious sheet according to Comparative Example 1 was made under the same conditions as those for Inventive Example 1 except that a length of respective bosses was dimensioned to be 0.5 mm.

Comparative Example 2

The liquid-pervious sheet according to Comparative Example 2 was made under the same conditions as those for Inventive Example 2 except that a length of respective bosses was dimensioned to be 0.5 mm.

Comparative Example 3

The liquid-pervious sheet according to Comparative Example 3 was made under the same conditions as those for Inventive Example 5 except that none of the compressed debosses was formed. This liquid-pervious sheet corresponds to the first nonwoven fabric 130a of FIG. 10.

TABLE 1

| | | Inventive Example 1 | Inventive Example 2 | Inventive Example 3 | Inventive Example 4 | Comparative Example 1 | Comparative Example 2 | Comparative Example 3 |
|---|---|---|---|---|---|---|---|---|
| Height of boss (mm) | | 3.0 | 3.0 | 0.5 | 0.5 | 0.5 | 0.5 | — |
| One side length in each skin-contactable area (mm) | | 9 | 6 | 18 | 12 | 9 | 6 | — |
| Evaluation items | unit | | | | | | | |
| Q-max value | kw/m$^2$ | 0.07 | 0.06 | 0.07 | 0.09 | 0.08 | 0.10 | 0.15 |
| Remaining quantity | g | 0.00 | 0.00 | 0.04 | 0.04 | 0.01 | 0.00 | 0.04 |
| Wipe-off efficiency | % | 100 | 100 | 96.0 | 96.0 | 98.6 | 100 | 96.4 |
| Softness of texture | rank | A | A | A | A | B | C | A |
| Thickness of 1st topsheet under load | mm | 0.9 | 0.9 | 0.9 | 0.8 | 0.6 | 0.5 | 1.2 |

The evaluation result suggests that the liquid-pervious sheets as the inventive examples which are formed with the compressed debosses in addition to the crests and the troughs are superior to the liquid-pervious sheet according to the Comparative Example 3 which is formed with the crests and the troughs but none of the compressed debosses in the efficiency at which bodily fluids wetting the diaper's skin can be wiped off. The evaluation result suggests also that the height of the bosses may be set to be relatively long or, if the bosses are relatively short, the length of one side of the skin-contactable area may be enlarged to assure that the thickness of the first topsheet, i.e., the height of the crests in the first topsheet can maintain 60% or more of the height of the crests before the debossing treatment. In this way, high evaluation result was obtained from such test pieces with respect to softness of texture.

Generally, with respect to a baby who is newborn to four months old, voided volume is as small as about 20 ml and a flow velocity of urine is relatively low. In addition, such a baby lies down almost entire time and, inconsequence, urine discharged from the urethral orifice often flows along the baby's skin and rarely discharged from the urethral orifice toward the diaper. As a countermeasure against the urine flowing along the baby's skin, the diaper providing a high wiping off efficiency is preferably put on the baby's body so that the topsheet of the diaper may wipe-off urine as the topsheet comes in contact with the baby's skin and the urine wiped off in this manner may be absorbed by the diaper. As demonstrated by the inventive examples in Table 1, the topsheet according to the present invention is superior in the wiping off efficiency for urine and in the soft feel against the diaper wearer's skin, and therefore suitable as the topsheet of the disposable diaper exclusively for the baby who is earlier months old.

The first aspects described above may be arranged in at least the following items:
(i) A liquid-pervious sheet having a longitudinal direction, a transverse direction and a thickness direction being orthogonal to one another and including a nonwoven fabric of thermoplastic synthetic fibers; wherein both surfaces of the liquid-pervious sheet intersect with the thickness direction and extend in the longitudinal direction and the transverse direction; and one of the both surfaces is formed with crests and troughs extending in the longitudinal direction and alternating in the transverse direction to form an undulated surface having repeated undulations; and the other of the both surfaces being formed to be a flat surface, wherein:

at least in the crests, the undulated surface includes dot-like debosses formed by locally compressing the nonwoven fabric from the undulated surface toward the opposite surface; and the thermoplastic synthetic fibers in the nonwoven fabric more densely gather together in the debosses and in zones underlying respective the debosses than in zones surrounding the debosses wherein the fiber-form of each of the thermoplastic fibers is maintained.
(xi) A method of making a liquid-pervious sheet having a longitudinal direction, a transverse direction and a thickness direction being orthogonal to one another and including a nonwoven fabric of thermoplastic synthetic fibers wherein both surfaces of the liquid-pervious sheet intersect with the thickness direction and extend in the longitudinal direction and the transverse direction; and one of the surfaces is formed with crests and troughs extending in the longitudinal direction and alternating in the transverse direction to form an undulated surface having repeated undulations; the other of the both surfaces being formed to be a flat surface, the method including:

a. continuously feeding a web as mass of thermoplastic synthetic fibers loaded on an air-permeable support means and in a machine direction and subjecting the web to pressurized air jets or pressurized water jets ejected by a series of nozzles arranged in a cross direction intersecting with the machine direction above the support means, so that the pressurized air or the pressurized water may be directed from one surface of the web to the other surface, to form the one surface of the web with crests and troughs extending in parallel to one another in the machine direction and alternating in the cross direction to form repeated undulations;

b. feeding the web formed with the crests and the troughs into a clearance between a pair of debossing rolls including a roll having a smooth peripheral surface and a roll having a series of bosses on a peripheral surface thereof so that the bosses may work on the web in a direction from the undulated surface toward the opposite surface thereof and thereby locally compressing the web from the undulated surface toward the opposite surface thereof to form dot-like debosses at least in the crests; and c. keeping the bosses at a temperature in a range to maintain a surface temperature of the bosses without melting the surfaces of the thermoplastic synthetic fibers.

One or more aspect described in the above item (i) may provide one or more of the following advantageous effects:
(a) The liquid-pervious sheet according to the present invention on the first aspect thereof is formed at least in the crests with the debosses. In the respective debosses, the thermoplastic synthetic fibers in the nonwoven fabric forming the liquid-pervious sheet more densely gather together than in the zones surrounding the respective debosses and thereby maintain the initial fibrous configuration thereof. Consequently, bodily fluids once absorbed by the crests smoothly move not only to the troughs but also to the debosses and do not stay in the respective crests.

One or more aspect described in the above item (xi) may provide one or more of the following advantageous effects:
(b) In the method of making the liquid-pervious sheet according to the present invention on the second aspect thereof, the surface temperature of the bosses is kept at a temperature in a range which will not melt the surfaces of the thermoplastic synthetic fibers in the nonwoven fabric. Consequently, in the respective debosses formed by these bosses, the thermoplastic synthetic fibers are kept in close contact one another but not fusion-bonded together due to the debossing treatment.

Additionally, one or more of the following embodiments are provided in accordance with further aspects:
(ii) The compressed debosses are included also in the respective crests.
(iii) A series of the compressed debosses are arranged in a direction diagonally intersecting with the crests and the troughs to form rows and the rows comprise a plurality of first rows extending in parallel to one another in the direction diagonally intersecting with the crests and the troughs and a plurality of second rows intersecting with the first rows and extending in parallel to one another in the direction diagonally intersecting with the crests and the troughs.
(iv) A pair of the adjacent first rows intersects with each pair of the adjacent second rows to form the first surface with a skin-contactable area surrounded by the first rows and the second rows and the skin-contactable area includes at least one row of the crests.
(v) The skin-contactable area has a dimension in the longitudinal direction larger than a dimension in the transverse direction.
(vi) Each of the thermoplastic synthetic fibers in the nonwoven fabric is a staple fiber having fineness in a range of 1 to 4 dtex, a fiber length in a range of about 30 to about 60 mm and a mass per unit area in a range of about 10 to about 50 g/m$^2$.
(vii) A liquid-pervious fibrous layer formed of thermoplastic synthetic fibers is bonded to the opposite surface of the liquid-pervious sheet, the fibrous layer is formed with second compressed debosses respectively aligned the compressed debosses in the thickness direction and, in the second compressed debosses, the thermoplastic synthetic fibers in the fibrous layer more densely gather together than in zones surrounding respective the second compressed debosses and thereby maintain initial fiber formation of the respective thermoplastic synthetic fibers.

(viii) Each of the thermoplastic synthetic fibers forming the fibrous layer is a staple fiber or a filament having fineness in a range of 1 to 4 dtex and a mass per unit area in a range of about 10 to about 50 g/m².

(ix) The liquid-pervious sheet has a Q-max value of 0.10 kw/m² or less as measured after artificial urine has been wiped off in artificial urine wiping off test.

(x) The liquid-pervious sheet is used as a topsheet of the disposable diaper for a baby who is less than six months old.

(xii) the one surface is formed by the bosses with a plurality of the compressed debosses so as to define two or more first rows of the compressed debosses extending in parallel to one another in a direction diagonally intersecting with the crests and the troughs and two or more second rows of the compressed debosses diagonally intersecting with the two or more first rows and extending in parallel to one another in a direction intersecting with the crests and the troughs.

(xiii) A liquid-pervious fibrous layer comprising staple fibers or filaments of thermoplastic synthetic fibers is bonded to the opposite surface of the web having been formed with the crests and the troughs with hot melt adhesive to form a composite web which is, in turn, fed into a clearance between a pair of the rolls to obtain the liquid-pervious sheet including the fibrous layer.

(xiv) Each of the bosses has a length exceeding a thickness of the composite web.

According to the embodiments in the above (ii) to (x), the advantageous effect (s) set forth at (a) is/are better ensured.

According to the embodiments in the above (xii) to (xiv), the advantageous effect (s) set forth at (b) is/are better ensured.

Further advantageous effects of the respective embodiments may be obtained as discussed in the respective related descriptions.

The invention claimed is:

1. A liquid-pervious sheet having a longitudinal direction, a transverse direction and a thickness direction being orthogonal to one another, and comprising a nonwoven fabric made of thermoplastic synthetic fibers; wherein both surfaces of a liquid-pervious sheet intersect with the thickness direction and extend in the longitudinal direction and the transverse direction; and one of the surfaces includes protruding crests and recessed troughs extending in the longitudinal direction and alternating in the transverse direction to form an undulated surface having repeated undulations; the other of the surfaces being formed to be a flat surface, wherein:
at least in the crests, the undulated surface includes dot-like debosses formed by locally compressing the nonwoven fabric from the undulated surface toward the opposite surface thereof without melting the thermoplastic fibers to the extent that they lose their initial fibrous configuration; and
the thermoplastic synthetic fibers in the nonwoven fabric more densely gather together in the debosses and in zones underlying respective the debosses than in zones surrounding the debosses wherein the fiber-form of each of the thermoplastic fibers is maintained.

2. The liquid-pervious sheet defined by claim 1, wherein the compressed debosses are included also in apexes of the crests.

3. The liquid-pervious sheet defined by claim 2, wherein a series of the debosses are arranged in directions diagonally intersecting with the crests and the troughs to form rows; and the rows comprise: a plurality of first rows extending in parallel to one another in the direction diagonally intersecting with the crests and the troughs; and a plurality of second rows intersecting with the first rows and extending in parallel to one another in the direction diagonally intersecting with the crests and the troughs.

4. The liquid-pervious sheet defined by claim 3, wherein a pair of adjacent the first rows intersects with each pair of adjacent the second rows to form a skin-contactable area surrounded by the first rows and the second rows and the skin-contactable area includes at least one of the crests.

5. The liquid-pervious sheet defined by claim 4, wherein the skin-contactable area has a dimension in the longitudinal direction larger than a dimension in the transverse direction.

6. The liquid-pervious sheet defined by claim 3, wherein each of the thermoplastic synthetic fibers in the nonwoven fabric is a staple fiber having a fineness in a range of 1 to 4 dtex, a fiber length in a range of 30 to 60 mm and a mass per unit area in a range of 10 to 50 g/m².

7. The liquid-pervious sheet defined by claim 2, wherein each of the thermoplastic synthetic fibers in the nonwoven fabric is a staple fiber having a fineness in a range of 1 to 4 dtex, a fiber length in a range of 30 to 60 mm and a mass per unit area in a range of 10 to 50 g/m².

8. The liquid-pervious sheet defined by claim 1, wherein a series of the debosses are arranged in directions diagonally intersecting with the crests and the troughs to form rows; and the rows comprise: a plurality of first rows extending in parallel to one another in the direction diagonally intersecting with the crests and the troughs; and a plurality of second rows intersecting with the first rows and extending in parallel to one another in the direction diagonally intersecting with the crests and the troughs.

9. The liquid-pervious sheet defined by claim 8, wherein a pair of adjacent the first rows intersects with each pair of adjacent the second rows to form a skin-contactable area surrounded by the first rows and the second rows and the skin-contactable area includes at least one of the crests.

10. The liquid-pervious sheet defined by claim 9, wherein the skin-contactable area has a dimension in the longitudinal direction larger than a dimension in the transverse direction.

11. The liquid-pervious sheet defined by claim 8, wherein each of the thermoplastic synthetic fibers in the nonwoven fabric is a staple fiber having a fineness in a range of 1 to 4 dtex, a fiber length in a range of 30 to 60 mm and a mass per unit area in a range of 10 to 50 g/m².

12. The liquid-pervious sheet defined by claim 1, wherein each of the thermoplastic synthetic fibers in the nonwoven fabric is a staple fiber having a fineness in a range of 1 to 4 dtex, a fiber length in a range of 30 to 60 mm and a mass per unit area in a range of 10 to 50 g/m².

13. The liquid-pervious sheet defined by claim 12, wherein the liquid-pervious sheet has a Q-max value of 0.10 kW/m² or less as measured after artificial urine has been wiped off in artificial urine wiping off test.

14. The liquid-pervious sheet defined by claim 1, wherein a liquid-pervious fibrous layer formed of thermoplastic synthetic fibers is bonded to the opposite surface of the liquid-pervious sheet; the fibrous layer is formed with second debosses respectively aligned with the debosses in the thickness direction; and in the second debosses, the thermoplastic synthetic fibers in the fibrous layer are more densely gathered together than in zones surrounding respective the second debosses and thereby maintain the fiber configuration of the thermoplastic synthetic fibers.

15. The liquid-pervious sheet defined by claim 14, wherein each of the thermoplastic synthetic fibers forming the fibrous layer is a staple fiber or a filament having fineness in a range of 1 to 4 dtex and a mass per unit area (basis mass) in a range of 10 to 50 g/m².

16. The liquid-pervious sheet defined by claim 1, wherein the liquid-pervious sheet is used as a topsheet of disposable diaper for a baby who is less than six months old.

\* \* \* \* \*